(12) United States Patent
Brown et al.

(10) Patent No.: US 7,988,717 B2
(45) Date of Patent: *Aug. 2, 2011

(54) LONGITUDINALLY FLEXIBLE EXPANDABLE STENT

(75) Inventors: Brian J. Brown, Hanover, MN (US); Michael Davis, Shorewood, MN (US); David Friesen, Brooklyn Park, MN (US); Timothy J. Ley, Shoreview, MN (US); Sean P. Skubitz, Shoreview, MN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 1200 days.

This patent is subject to a terminal disclaimer.

(21) Appl. No.: 10/705,273

(22) Filed: Nov. 10, 2003

(65) Prior Publication Data

US 2004/0181276 A1  Sep. 16, 2004

Related U.S. Application Data

(63) Continuation of application No. 09/197,278, filed on Nov. 20, 1998, now Pat. No. 7,204,848, which is a continuation-in-part of application No. 08/511,076, filed on Aug. 3, 1995, now Pat. No. 6,818,014, which is a continuation-in-part of application No. 08/396,569, filed on Mar. 1, 1995, now abandoned.

(51) Int. Cl.
*A61F 2/06* (2006.01)
*A61F 11/00* (2006.01)
(52) U.S. Cl. .................. 623/1.15; 606/108; 606/194
(58) Field of Classification Search .............. 623/1.15, 623/1.11; 606/194, 195, 198
See application file for complete search history.

(56) References Cited

U.S. PATENT DOCUMENTS

| | | | |
|---|---|---|---|
| 2,836,181 A | 5/1958 | Tapp | |
| 3,105,492 A | 10/1963 | Jeckel | |
| 3,272,204 A | 9/1966 | Artandi et al. | |
| 3,490,975 A | 1/1970 | Lightwood et al. | |
| 3,509,883 A | 5/1970 | Dibelius | |
| 3,526,228 A | 9/1970 | Lyng | |
| 3,562,820 A | 2/1971 | Braun | |
| 3,635,215 A | 1/1972 | Shea et al. | |
| 3,657,744 A | 4/1972 | Ersek | |
| 3,771,526 A | 11/1973 | Rudie | |
| 3,868,956 A | 3/1975 | Alfidi et al. | |
| 3,993,078 A | 11/1976 | Bergentz et al. | |
| 4,078,167 A | 3/1978 | Banas et al. | |
| 4,127,761 A | 11/1978 | Pauley et al. | |
| 4,130,904 A | 12/1978 | Whalen | |
| 4,140,126 A | 2/1979 | Choudhury | |

(Continued)

FOREIGN PATENT DOCUMENTS

DE  297 01 758  3/1997
(Continued)

OTHER PUBLICATIONS

U.S. Appl. No. 60/076,946, filed Mar. 5, 1998, Tseng et al.
(Continued)

*Primary Examiner* — Vy Q Bui
(74) *Attorney, Agent, or Firm* — Vidas, Arrett & Steinkraus, P.A.

(57) ABSTRACT

Segmented articulatable stent of open structure comprised of end-connected struts of first and second lengths making up first and second segments with angular interconnects between adjacent first and second segments.

23 Claims, 17 Drawing Sheets

U.S. PATENT DOCUMENTS

| | | | |
|---|---|---|---|
| 4,141,364 A | 2/1979 | Schultze | |
| 4,164,045 A | 8/1979 | Bokros et al. | |
| 4,214,587 A | 7/1980 | Sakura, Jr. | |
| 4,300,244 A | 11/1981 | Bokros | |
| 4,313,231 A | 2/1982 | Koyamada | |
| 4,319,363 A | 3/1982 | Ketharanathan | |
| 4,425,908 A | 1/1984 | Simon | |
| 4,441,215 A | 4/1984 | Kaster | |
| 4,470,407 A | 9/1984 | Hussein | |
| 4,501,264 A | 2/1985 | Rockey | |
| 4,503,569 A | 3/1985 | Dotter | |
| 4,512,338 A | 4/1985 | Balko et al. | |
| 4,535,770 A | 8/1985 | Lemole | |
| 4,550,447 A | 11/1985 | Seiler, Jr. et al. | |
| 4,553,545 A | 11/1985 | Maass et al. | |
| 4,560,374 A | 12/1985 | Hammerslag | |
| 4,580,568 A | 4/1986 | Gianturco | |
| 4,597,389 A | 7/1986 | Ibrahim et al. | |
| 4,647,416 A | 3/1987 | Seiler, Jr. et al. | |
| 4,649,922 A | 3/1987 | Wiktor | |
| 4,655,771 A | 4/1987 | Wallsten | |
| 4,655,776 A | 4/1987 | Lesinski | |
| 4,665,918 A | 5/1987 | Garza et al. | |
| 4,681,110 A | 7/1987 | Wiktor | |
| 4,693,721 A | 9/1987 | Ducheyne | |
| 4,733,665 A | 3/1988 | Palmaz | |
| 4,739,762 A | 4/1988 | Palmaz | |
| 4,740,207 A | 4/1988 | Kreamer | |
| 4,760,849 A | 8/1988 | Kropf | |
| 4,762,128 A | 8/1988 | Rosenbluth | |
| 4,769,029 A | 9/1988 | Patel | |
| 4,771,773 A | 9/1988 | Kropf | |
| 4,776,337 A | 10/1988 | Palmaz | |
| 4,786,507 A | 11/1988 | Schmidt | |
| 4,787,899 A | 11/1988 | Lazarus | |
| 4,795,458 A | 1/1989 | Regan | |
| 4,795,465 A | 1/1989 | Marten | |
| 4,800,882 A | 1/1989 | Gianturco | |
| 4,820,298 A | 4/1989 | Leveen et al. | |
| 4,830,003 A | 5/1989 | Wolff et al. | |
| 4,842,575 A | 6/1989 | Hoffman, Jr. et al. | |
| 4,848,343 A | 7/1989 | Wallsten et al. | |
| 4,851,009 A | 7/1989 | Pinchuk | |
| 4,856,516 A | 8/1989 | Hillstead | |
| 4,872,874 A | 10/1989 | Taheri | |
| 4,877,030 A | 10/1989 | Beck et al. | |
| 4,878,906 A | 11/1989 | Lindemann et al. | |
| 4,886,062 A | 12/1989 | Wiktor | |
| 4,913,141 A | 4/1990 | Hillstead | |
| 4,922,905 A | 5/1990 | Strecker | |
| 4,950,227 A | 8/1990 | Savin et al. | |
| 4,950,258 A | 8/1990 | Kawai et al. | |
| 4,994,071 A | 2/1991 | MacGregor | |
| 5,015,253 A | 5/1991 | MacGregor | |
| 5,019,090 A | 5/1991 | Pinchuk | |
| 5,035,706 A | 7/1991 | Giantureo et al. | |
| 5,037,392 A | 8/1991 | Hillstead | |
| 5,059,211 A | 10/1991 | Stack et al. | |
| 5,064,435 A | 11/1991 | Porter | |
| 5,091,211 A | 2/1992 | Richard | 427/44 |
| 5,092,877 A | 3/1992 | Pinchuk | |
| 5,102,417 A | 4/1992 | Palmaz | |
| 5,104,399 A | 4/1992 | Lazarus | |
| 5,104,404 A | 4/1992 | Wolff | |
| 5,108,415 A | 4/1992 | Pinchuk et al. | |
| 5,108,417 A | 4/1992 | Sawyer | |
| 5,122,154 A | 6/1992 | Rhodes | |
| 5,133,732 A | 7/1992 | Wiktor | |
| 5,135,536 A | 8/1992 | Hillstead | |
| 5,139,480 A | 8/1992 | Hickle et al. | |
| 5,147,385 A | 9/1992 | Beck et al. | |
| 5,147,400 A | 9/1992 | Kaplan et al. | |
| 5,158,548 A | 10/1992 | Lau et al. | |
| 5,163,952 A | 11/1992 | Froix | |
| 5,195,984 A | 3/1993 | Schatz | |
| 5,197,978 A | 3/1993 | Hess | |
| 5,217,483 A | 6/1993 | Tower | |
| 5,226,913 A | 7/1993 | Pinchuk | |
| 5,282,823 A | 2/1994 | Schwartz et al. | |
| 5,282,824 A | 2/1994 | Gianturco | |
| 5,292,331 A | 3/1994 | Boneau | |
| 5,304,200 A | 4/1994 | Spaulding | |
| 5,344,425 A | 9/1994 | Sawyer | |
| 5,354,308 A | 10/1994 | Simon et al. | |
| 5,354,309 A | 10/1994 | Schnepp-Pesch et al. | |
| 5,383,892 A | 1/1995 | Cardon et al. | |
| 5,405,377 A | 4/1995 | Cragg | |
| 5,411,552 A | 5/1995 | Andersen et al. | 623/2 |
| 5,449,373 A | 9/1995 | Pinchasik et al. | |
| 5,591,197 A | 1/1997 | Orth et al. | 606/198 |
| 5,649,952 A | 7/1997 | Lam | 606/198 |
| 5,707,386 A | 1/1998 | Schnepp-Pesch et al. | 606/194 |
| 5,718,713 A | 2/1998 | Frantzen | 606/198 |
| 5,735,893 A | 4/1998 | Lau et al. | 623/1 |
| 5,741,317 A | 4/1998 | Ostrow | 3/1 |
| 5,741,327 A | 4/1998 | Frantzen | 623/1 |
| 5,755,776 A | 5/1998 | Al-Saadon | 623/1 |
| 5,755,781 A | 5/1998 | Jayaraman | 623/1 |
| 5,776,161 A | 7/1998 | Globerman | 606/194 |
| 5,776,183 A | 7/1998 | Kanesaka et al. | 623/1 |
| 5,800,521 A | 9/1998 | Orth | 623/1 |
| 5,807,404 A | 9/1998 | Richter | 623/1 |
| 5,810,872 A * | 9/1998 | Kanesaka et al. | 623/1.15 |
| 5,824,059 A | 10/1998 | Wijay | 623/1 |
| 5,827,321 A * | 10/1998 | Roubin et al. | 623/1.16 |
| 5,836,966 A | 11/1998 | St. Germain | 606/198 |
| 5,876,432 A | 3/1999 | Lau et al. | 623/1 |
| 5,911,754 A | 6/1999 | Kanesaka et al. | 623/1 |
| 5,922,021 A | 7/1999 | Jang | 623/1 |
| 5,925,061 A | 7/1999 | Ogi et al. | 606/198 |
| 5,938,697 A | 8/1999 | Killion et al. | 623/1 |
| 5,948,016 A | 9/1999 | Jang | 623/1 |
| 5,954,743 A | 9/1999 | Jang | 606/198 |
| 6,017,365 A | 1/2000 | Von Oepen | 623/1 |
| 6,042,597 A | 3/2000 | Kveen et al. | 606/198 |
| 6,056,775 A | 5/2000 | Borghi et al. | 623/1.16 |
| 6,068,656 A | 5/2000 | Von Oepen | 623/1.17 |
| 6,106,548 A | 8/2000 | Roubin et al. | 623/1.15 |
| 6,129,755 A | 10/2000 | Mathis et al. | 623/1.15 |
| 6,132,460 A | 10/2000 | Thompson | 623/1.15 |
| 6,190,403 B1 * | 2/2001 | Fischell et al. | 623/1.16 |
| 6,261,319 B1 | 7/2001 | Kveen et al. | 623/1.15 |
| 6,340,366 B2 | 1/2002 | Wijay | 623/1.13 |
| 6,355,057 B1 | 3/2002 | DeMarais et al. | 623/1.15 |
| 6,358,274 B1 | 3/2002 | Thompson | 623/1.15 |
| 6,461,380 B1 * | 10/2002 | Cox | 623/1.17 |
| 6,471,720 B1 | 10/2002 | Ehr et al. | 623/1.15 |
| 6,488,703 B1 | 12/2002 | Kveen et al. | 623/1.15 |
| 6,520,987 B1 | 2/2003 | Plante | 623/1.16 |
| 6,533,808 B1 | 3/2003 | Thompson | 623/1.15 |
| 6,540,775 B1 | 4/2003 | Fischell et al. | 623/1.15 |
| 6,540,777 B2 | 4/2003 | Stenzel | 623/1.16 |
| 6,613,081 B2 | 9/2003 | Kim et al. | 623/1.15 |
| 6,776,793 B2 | 8/2004 | Brown et al. | 623/1.15 |

FOREIGN PATENT DOCUMENTS

| | | |
|---|---|---|
| DE | 297 02 671 U1 | 4/1997 |
| DE | 297 08 689 U1 | 7/1997 |
| DE | 297 08 879 U1 | 7/1997 |
| DE | 29708879 | 9/1997 |
| DE | 297 16 476 U1 | 2/1998 |
| DE | 298 16 878 U1 | 12/1998 |
| EP | 0 364 737 B1 | 4/1990 |
| EP | 0 540 290 A2 | 5/1993 |
| EP | 0 541 443 A1 | 5/1993 |
| EP | 0 606 165 A1 | 7/1994 |
| EP | 0 821 920 A1 | 2/1998 |
| EP | 0 876 806 A1 | 11/1998 |
| EP | 0897698 | 2/1999 |
| EP | 0970664 | 1/2000 |
| EP | 0983753 | 3/2003 |
| JP | 6-4175 | 3/1994 |
| WO | WO 94/17754 | 8/1994 |
| WO | 96/26689 | 9/1996 |
| WO | 9628116 | 9/1996 |
| WO | 97/04721 | 2/1997 |
| WO | 97/14375 | 2/1997 |

| | | |
|---|---|---|
| WO | 97/25937 | 7/1997 |
| WO | 97/32543 | 9/1997 |
| WO | 97/32544 | 9/1997 |
| WO | 97/33534 | 9/1997 |
| WO | 97/40780 | 11/1997 |
| WO | 97/40781 | 11/1997 |
| WO | 97/40782 | 11/1997 |
| WO | 97/40783 | 11/1997 |
| WO | 97/40874 | 11/1997 |
| WO | 97/45073 | 12/1997 |
| WO | 98/20810 | 5/1998 |
| WO | 99/44535 | 9/1999 |

OTHER PUBLICATIONS

U.S. Appl. No. 09/623,347, filed Nov. 15, 2000, Tseng et al.
U.S. Appl. No. 10/474,848, filed Dec. 29, 2003, Tseng et al.
U.S. Appl. No. 09/197,278, filed Nov. 20, 1998, Brown et al.
U.S. Appl. No. 08/511,076, filed Aug. 3, 1995, Brown et al.
U.S. Appl. No. 08/396,569, filed Mar. 1, 1995, Brown et al.
Beyar et al, "The BeStent: The Parallel-Serial Jang Stents", *Handbook of Coronary Steats, Second Edition*, 158-171 & 229-234 (1998).
Beyar et al, "Newer Stents: Materials and Designs", *IAGS Proceedings*, 9(5): 363-371 (Jun. 1997).
Roguin et al, "Acute and 30-Day Results of the Serpentine Balloon Expandable Stent Implantation in Simple and Complex Coronary Arterial Narrowings", *The American Journal of Cardiology*, 80:1155.1162 (Nov. 1997).
Roguin et al, "beStent—the serpentine balloon expandable stent: review of mechanical properties and clinical experience". *Artif Organs*, 22(3):243-249 (Mar. 1998).
*A View of Vascular Stents*, by Richard A. Schatz, MD, From the Arizona Heart Institute Foundation, Phoenix, Arizona, *Circulation*, vol. 79, No. 2, Feb. 1989, pp. 445-457.
Japanese Infringement Search on Articulated Expandable Stents, Dated Jul. 12. 1993.
Improved Dilation Catheter Balloons. by Stanley D. Levy, Ph.D. *Journal of Clinical Engineering*, vol. 11. No. 4, Jul.-Aug. 1986, pp. 291-296.
Self-expanding Stainless Steel Biliary Stents, By Harold G. Coons, MD. *Radiology 1989*, vol. 170, No. Part 2. pp. 979-983.
Technical Note Entitled Modifications of Gianturco Expandable Wire Stents, by Barry T. Uchida et al., *AJR*, vol. 130, May 1988, pp. 1185-1187.
Expandable Biliary Endoprosthesis: An Experimental Study. By Carraseo et al., *AJR*, vol. 145, Dec. 1985, pp. 1279-1282.
Gianturco Expandable Metallic Biliary Stents: Results of a European Clinical Trial, By Irving, et al., *Interventional Radiology*, vol. 172, No. 2, Aug. 1989, pp. 321-326.
Tracheobronchial Tree: Expandable Metallic Stents Used in Experimetnal and Clinical Applications, Work In Progress, By Wallace et al., *Radiology*, Feb. 1986, pp. 309-312.

* cited by examiner

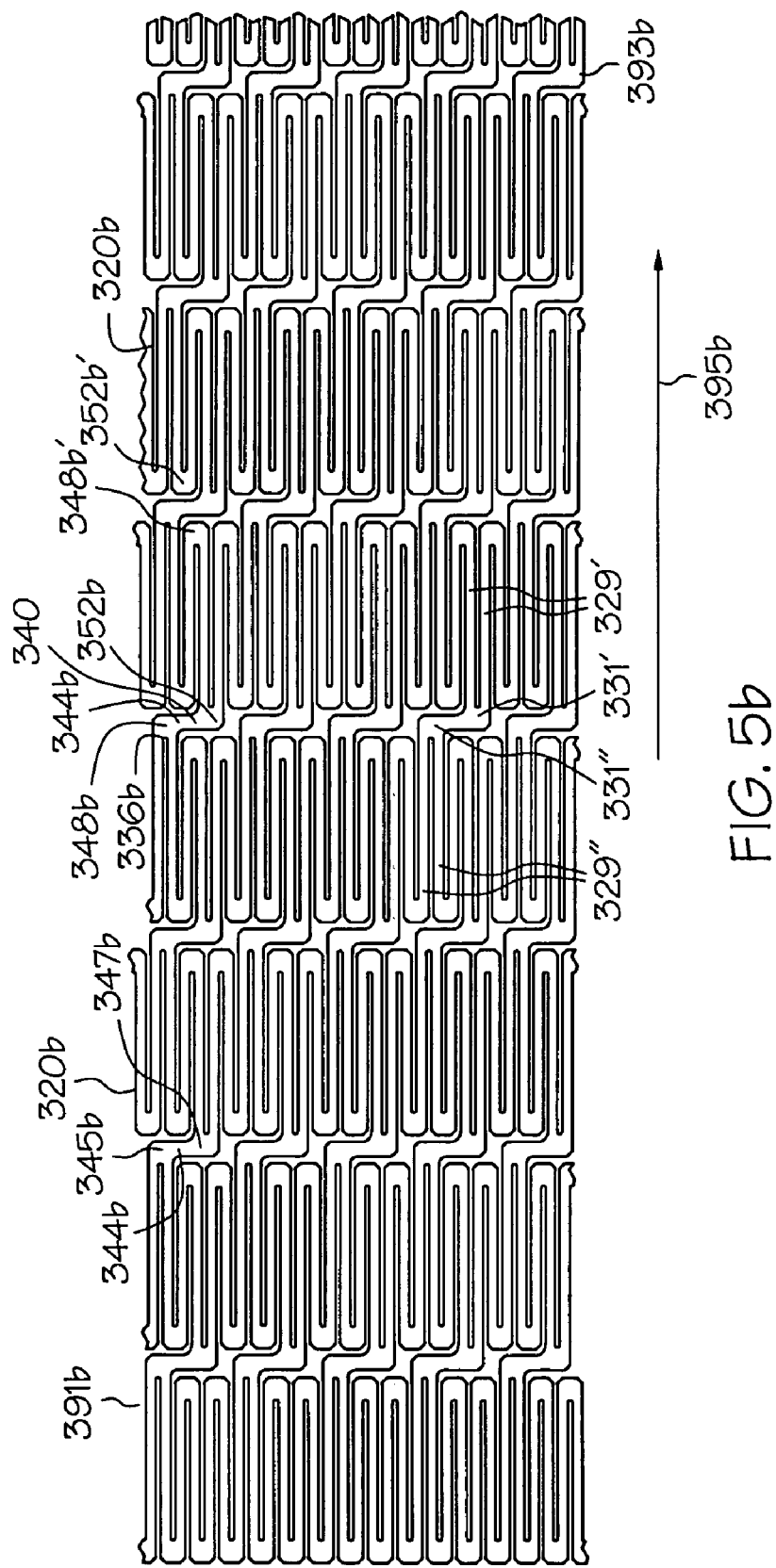

LONGITUDINALLY FLEXIBLE EXPANDABLE STENT

CROSS-REFERENCE TO RELATED APPLICATIONS

This application is a Continuation Application of U.S. application Ser. No. 09/197,278, filed Nov. 20, 1998, which is a Continuation-in-Part of application Ser. No. 08/511,076, filed Aug. 3, 1995, which is a Continuation-in-Part Application of U.S. application Ser. No. 08/396,569, filed Mar. 1, 1995 and now abandoned, the disclosure of all hereby incorporated by reference.

FIELD OF THE INVENTION

This invention relates to an endoprosthesis device for implantation within a body vessel, typically a blood vessel. More specifically, it relates to a tubular expandable stent of improved longitudinal flexibility.

BACKGROUND OF THE INVENTION

Stents are placed or implanted within a blood vessel for treating stenoses, strictures or aneurysms therein. They are implanted to reinforce collapsing, partially occluded, weakened, or dilated sections of a blood vessel. They have also been implanted in the urinary tract and in bile ducts.

Typically, a stent will have an unexpanded (closed) diameter for placement and an expanded (opened) diameter after placement in the vessel or the duct. Some stents are self-expanding and some are expanded mechanically with radial outward force from within the stent, as by inflation of a balloon.

An example of the latter type is shown in U.S. Pat. No. 4,733,665 to Palmaz, which issued Mar. 29, 1988, and discloses a number of stent configurations for implantation with the aid of a catheter. The catheter includes an arrangement wherein a balloon inside the stent is inflated to expand the stent by plastically deforming it, after positioning it within a blood vessel.

A type of self-expanding stent is described in U.S. Pat. No. 4,503,569 to Dotter which issued Mar. 12, 1985, and discloses a shape memory stent which expands to an implanted configuration with a change in temperature. Other types of self-expanding stents not made of shape memory material are also known.

This invention is directed to stents of all these types when configured so as to be longitudinally flexible as described in detail hereinbelow. Flexibility is a desirable feature in a stent so as to conform to bends in a vessel. Such stents are known in the prior art. Examples are shown in U.S. Pat. No. 4,856,516 to Hillstead; U.S. Pat. No. 5,104,404 to Wolff; U.S. Pat. No. 4,994,071 to MacGregor; U.S. Pat. No. 5,102,417 to Palmaz; U.S. Pat. No. 5,195,984 to Schatz; U.S. Pat. No. 5,135,536 to Hillstead; U.S. Pat. No. 5,354,309 to Shepp-Pesch et al.; EPO Patent Application 0 540 290 A2 to Lau; EPO Patent Application No. 0 364 787 B1 to Schatz, and PCT Application WO 94/17754 (also identified as German Patent Application 43 03 181).

Generally speaking, these kinds of stents are articulated and are usually formed of a plurality of aligned, expandable, relatively inflexible, circular segments which are interconnected by flexible elements to form a generally tubular body which is capable of a degree of articulation or bending. Unfortunately, a problem with such stents is that binding, overlapping or interference can occur between adjacent segments on the inside of a bend due to the segments moving toward each other and into contact or on the outside of a bend the segments can move away from each other, leaving large gaps. This can lead to improper vessel support, vessel trauma, flow disturbance, kinking, balloon burst during expansion, and difficult recross for devices to be installed through already implanted devices and to unsupported regions of vessel.

A diamond configuration with diagonal connections between each and every diamond of each segment is also known but such closed configurations lack flexibility.

It is an object of this invention to provide a longitudinally flexible stent of open configuration that avoids these problems and exhibits improved flexibility (radially and longitudinally) in the stent body segments thereof rather than in flexible joints between the segments.

It is a further object of the present invention to provide a stent that is flexible yet also allows for side branch access.

SUMMARY OF THE INVENTION

It is a goal of the present invention to provide a flexible stent formed of interconnected bands which provides for side branch access and which further avoids the problem of pinching or overlap between adjacent bands. Pinching or overlap is avoided where peaks and troughs of adjacent bands are circumferentially displaced relative to each other. The stents of the present invention accomplish this goal by having different bands characterized by different wavelengths over the length of the stent and/or disposing the interconnecting members in such a way that after expansion of the stent, the phase relationship between adjacent bands is altered with the peaks and troughs displaced circumferentially relative to each other.

The inventive expandable stents are formed of a plurality of interconnected band-like elements characterized by alternating peaks and troughs. The ends of the interconnecting members which join adjacent bands are circumferentially offset and optionally, longitudinally offset. Peaks and troughs in adjacent bands are circumferentially offset as well so that the stent, in an expanded state, will have minimal overlap of peaks and troughs.

To this end, the invention provides a tubular, flexible, expandable stent, comprising a plurality of undulating band-like elements of a selected wavelength or wavelengths. The band-like elements have peaks and troughs and are aligned on a common longitudinal axis to define a generally tubular stent body. The peaks and troughs take a generally longitudinal direction along the stent body. Adjacent band-like elements may be in phase or out of phase with each other. The inventive stents further comprise a plurality of interconnecting elements having first ends and second ends. The first and second ends extend from adjacent band-like elements and are displaced from one another in a longitudinal direction and in a radial direction along the stent. Desirably, upon expansion of the stent, at least some of the peaks and troughs of a given band-like element are displaced relative to each other about the periphery of the stent to accommodate longitudinal flexing of the stent within the band-like elements and without interference between adjacent band-like elements.

In one embodiment, two different types of band-like elements are present in the stent, first band-like elements with a first selected wavelength and second band-like elements with a second selected wavelength exceeding the first selected wavelength. The first and second band-like elements preferably alternate over the length of the stent. Although the terminology of 'first band-like element' and 'second band-like element' is used, it is not intended to convey the relative order of appearance of the elements in the inventive stents.

In another embodiment, two different types of band-like elements are present, first and second band-like elements, each of which has peaks and troughs. The first band-like elements have more peaks (or troughs) than the second band-like elements. Similarly, the invention is also directed to embodiments having first and second band-like elements with peaks and troughs where the peaks (or troughs) of the first band-like elements are spaced closer together than the peaks (or troughs) of the second band-like elements.

In another embodiment in which band-like elements of only one wavelength are present, adjacent bands are about 180° out of phase with one another. Interconnecting elements extend at an oblique angle relative to the longitudinal axis from a peak to a trough on an adjacent band.

In another embodiment in which band-like elements of only one wavelength are present, peaks from which interconnecting elements emanate are elongated relative to the peaks which are not connected to troughs and similarly, the troughs from which interconnectors emanate are elongated relative to troughs which are not connected to peaks. Further, each interconnecting element extends from the side of a peak to the side of a trough on an adjacent band.

In yet another embodiment in which band-like elements of only one wavelength are present, adjacent bands are about 90° out of phase with one another. Each interconnecting element extends between a peak and a trough and the ends of the interconnecting member are circumferentially offset from one another and, optionally, longitudinally offset.

The invention further provides a tubular, flexible, expandable stent having a longitudinal axis, comprising one or more cylindrical shaped first segments having first struts, the first segment being defined by a member formed in an undulating pattern of interconnected paired first struts and in which adjacent pairs of first struts in a given first segment are interconnected at opposite ends and one or more cylindrical shaped second segments defined by a member formed in an undulating pattern of interconnected paired second struts and in which adjacent pairs of second struts in a given second segment are interconnected at opposite ends. The first struts are shorter than the second struts. The first segments are formed of a number of first struts and the second segments are formed of a number of second struts with the number of first struts in a first segment exceeding the number of second struts in a second segment. The first and second segments, present and desirably alternating along the stent body, are aligned on a common longitudinal axis to define a generally tubular stent body. Adjacent first and second segments are connected by a plurality of interconnecting elements, each interconnecting element extending from an end of paired first struts on a first segment to an end of paired second struts on an adjacent second segment. The ends of interconnecting elements are circumferentially offset relative to each other, and optionally, longitudinally offset. Desirably, upon expansion of the stent, the paired struts of the adjacent segments are displaced relative to each other about the periphery of the stent body to accommodate longitudinal flexing of the stent within the segments and without interference between adjacent segments.

BRIEF DESCRIPTION OF THE FIGURES

FIG. 5b shows a flat view of a stent configuration according to the invention.

DETAILED DESCRIPTION OF THE INVENTION

While this invention may be embodied in many different forms, there are described in detail herein specific preferred embodiments of the invention. This description is an exemplification of the principles of the invention and is not intended to limit the invention to the particular embodiments illustrated.

Figure 1A:
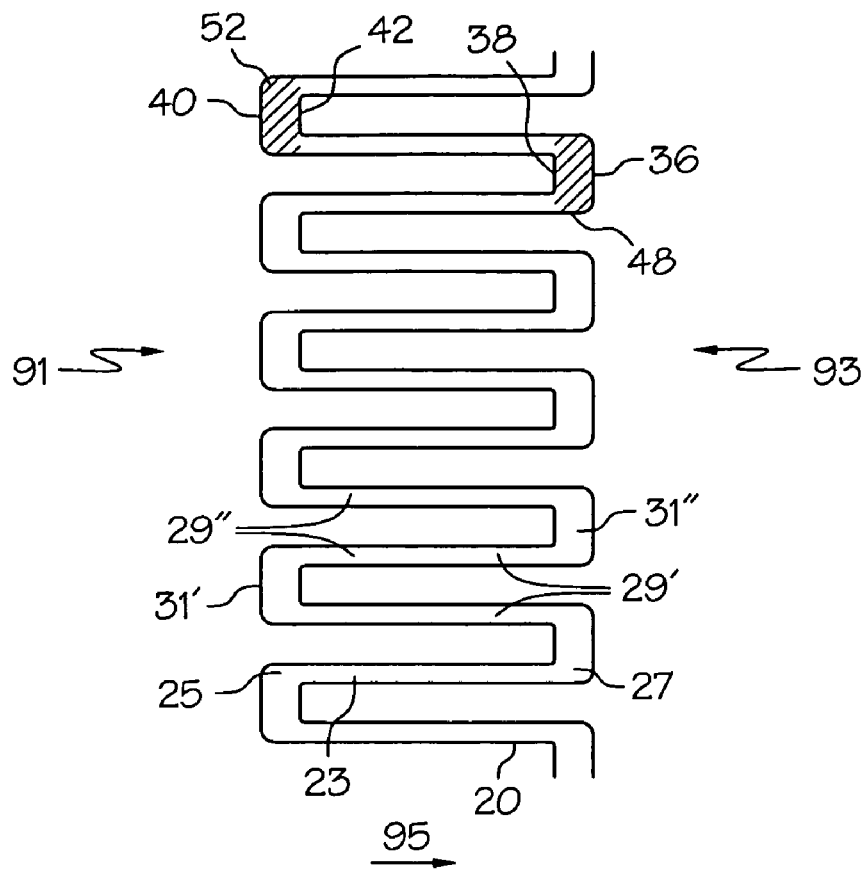
FIG. 1a shows a band-like element used in the inventive stents.
Figure 1B:
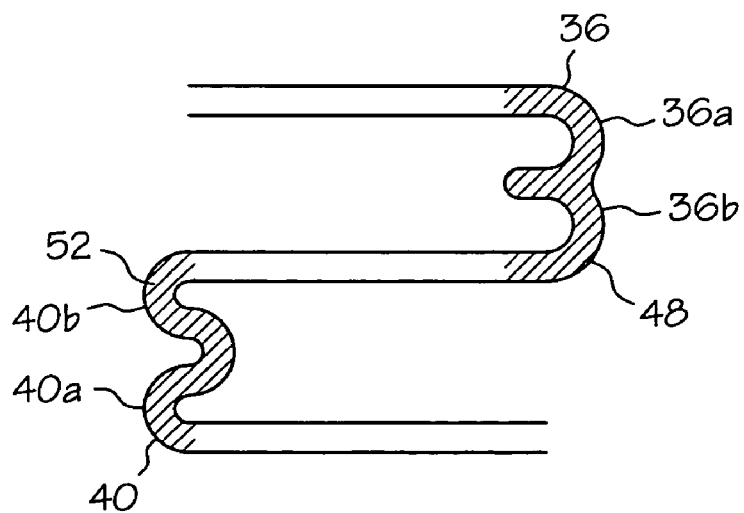
FIG. 1b shows a schematic of a peak region which contains a double peak and a trough region containing a double trough.

For the sake of consistency, the terms 'peak' and 'trough' shall be defined with respect to the proximal and distal ends of the stent. Each of the stents has a proximal end 91 and a distal end 93 and a longitudinal axis 95, as seen in FIG. 1a. Peaks 36 are generally concave relative to the proximal end of the stent and generally convex relative to the distal end of the stent. Troughs 40, on the other hand, are generally convex relative to the proximal end of the stent and generally concave relative to the distal end of the stent. Notwithstanding this definition, the term peak is also intended to extend to regions 48 that are generally peak-like which may, nevertheless, contain trough-like regions within the peak-like region as seen in FIG. 1b. Similarly the term trough is also intended to extend to regions 52 that are generally trough-like which may, nevertheless, contain peak-like regions within the trough-like region as seen in FIG. 1b.

Corresponding to each peak 36 is an inner diameter peak 38 where the inner diameter of the band-like element reaches its peak. The set of points on a given band-like element which are distal to inner diameter peak 38 is denoted peak region 48. Similarly, corresponding to each trough 40 is an inner diameter trough 42 where the inner diameter of the band-like element reaches its trough. The set of points on a given band-like element which are proximal to inner diameter trough 42 is denoted trough region 52. For the sake of clarity, unless otherwise indicated, analogous portions of stents will be similarly labeled, using three digit reference numerals to distinguish among the various embodiments shown.

Also included within this definition of peak regions and trough regions are peak regions which are comprised of multiple peaks as well as trough regions which are comprised of multiple troughs such as those shown schematically in FIG. 1*b*. Peak 36 is seen to consist of two sub-peaks 36*a,b* and trough 40 is similarly seen to consist of two sub-troughs 40*a,b*. In the case of peaks containing sub-peak and troughs containing sub-troughs, the peak region 48 includes all of the points along the band-like element between the sub-peaks that make up the peak and similarly, the trough region 52 includes all of the points along the band-like element between the sub-troughs that make up the trough.

The inventive stents may incorporate one or more bands of a chosen wavelength. In some embodiments, the inventive stents include one or more small amplitude, short wavelength bands to provide for flexibility and one or more large amplitude, long wavelength bands to give side branch access or to provide for sections of alternative strengths such as soft and/or stiff sections.

Figure 2:
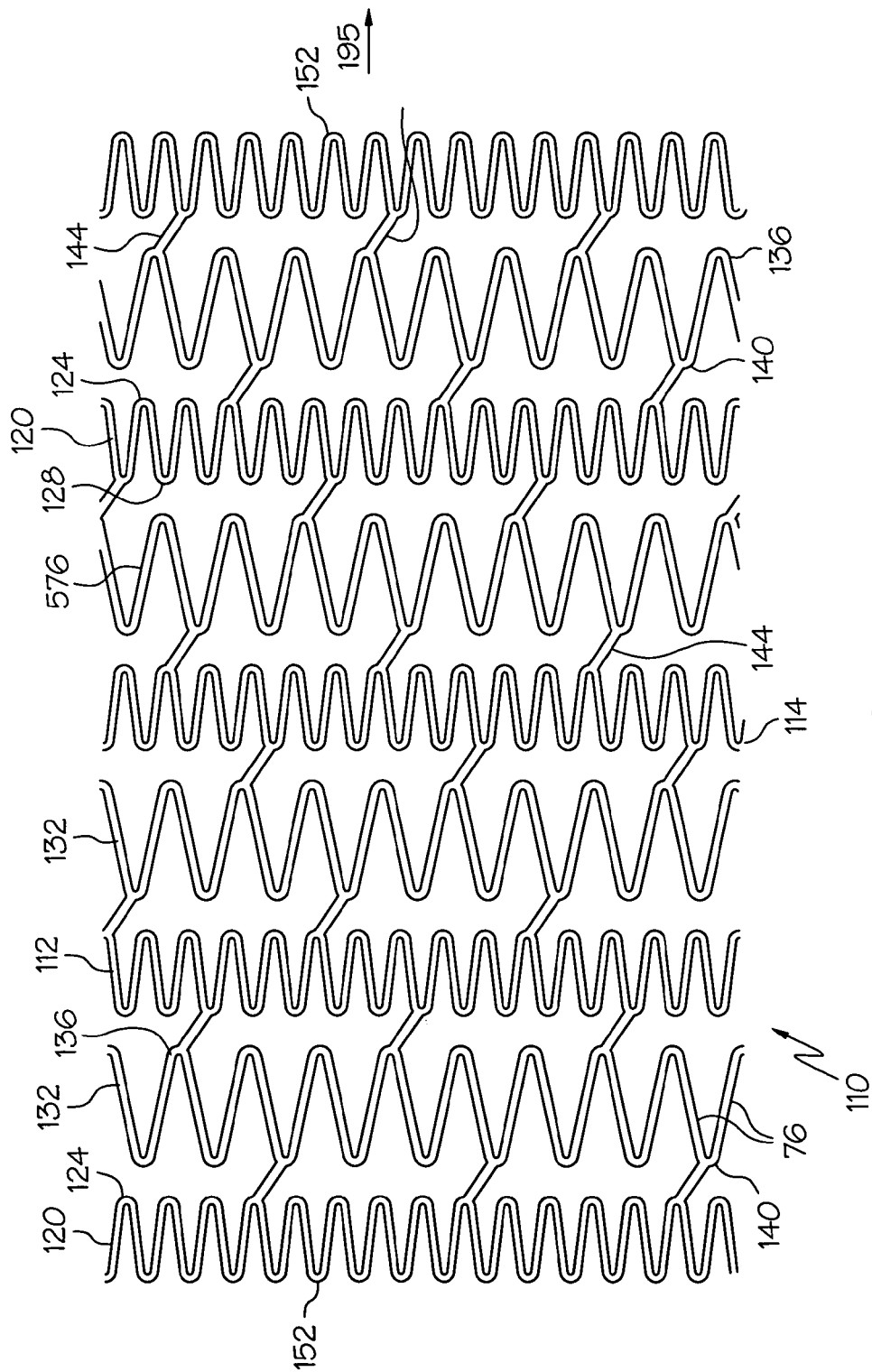
FIG. 2 shows a flat view of a stent configuration according to the invention.
Figure 3:
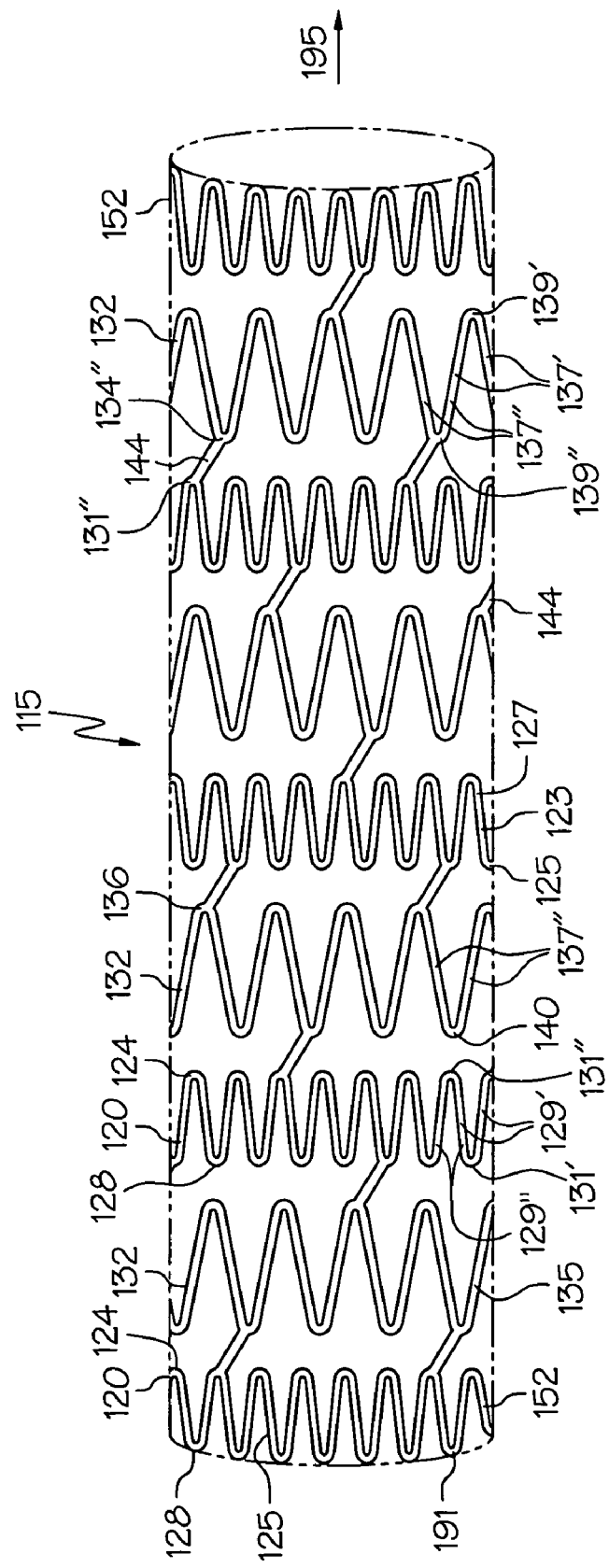
FIG. 3 shows the pattern of FIG. 2 in a tubular stent.

Turning to the Figures, FIG. 2 shows a flat view of a stent configuration and FIG. 3 shows the stent of FIG. 2 in tubular form. That is, the stent is shown for clarity in FIG. 2 in the flat and may be made from a flat pattern 110 (FIG. 2) which is formed into a tubular shape by rolling the pattern so as to bring edges 112 and 114 together (FIG. 2). The edges may then joined as by welding or the like to provide a cylindrical configuration such as that shown generally at 115 in FIG. 3.

A more preferred method of manufacture begins with a thin walled tube which is then laser cut to provide the desired configuration. It may also be chemically etched or EDM'd (electrical discharge machined) to form an appropriate configuration.

The configuration can be seen in these Figures to be made up of one or more spaced first band-like elements 120. First band-like elements have a generally serpentine configuration to provide continuous waves to the first band-like elements. The waves are characterized by a plurality of peaks 124 and troughs 128 taking a generally longitudinal direction along the cylinder such that the waves in first band-like elements 120 open as the stent is expanded from an unexpanded state having a first diameter to an expanded state having a second diameter.

The stent further comprises a plurality of spaced second band-like elements 132 having a generally serpentine configuration to provide continuous waves to the second band-like elements. The waves are characterized by a plurality of peaks 136 and troughs 140 taking a generally longitudinal direction along the cylinder such that the waves in the second band-like elements open as the stent is expanded from an unexpanded state having a first diameter to an expanded state having a second diameter. First and second band-like elements are characterized by respective wavelengths and amplitudes with the wavelength and amplitude of the second band-like elements exceeding the wavelength and amplitude of the first band-like elements.

Adjacent first band-like elements 120 and second band-like elements 132 are interconnected via a plurality of interconnecting elements 144. The ends of interconnecting element are circumferentially offset from each other.

In an embodiment, as shown in FIGS. 2 and 3, first band-like elements 120 and second band-like elements 132 alternate over the length of the stent. Optionally, as shown in FIGS. 2 and 3, each end 152 of the stent may terminate in a first band-like element. The invention also, however, contemplates each end terminating in a second band-like element, or further, one end terminating in a first band-like element and the other end terminating in a second band-like element.

While a minimum of one connecting element is required to join adjacent band-like elements, two or more interconnecting elements are preferred. In one embodiment, as shown in FIGS. 2 and 3, adjacent first and second band-like elements 120 and 132 are connected with three interconnecting elements 144. Further, in one embodiment, adjacent interconnecting elements 144 extending from peaks 136 on a first band-like element 120 are spaced five peaks apart on the first band-like element while adjacent interconnecting elements 144 extending from troughs 140 on a second band-like element 132 are spaced three troughs apart on the second band-like element.

It is a further feature of the present invention that peaks 124 on first band-like elements 120 are circumferentially displaced on the periphery of the stent from troughs 140 on adjacent second band-like elements 132. It is desirable that peaks and troughs be displaced in the expanded state of the stent to minimize the possibility of pinching or overlap between adjacent band-like elements.

Although the stent of FIG. 2 is comprised of two different wavelength band-like elements, the invention contemplates stents with a plurality of different wavelength band-like elements. As such, other stents may have three, four or more different wavelength band-like elements.

Figure 4A:
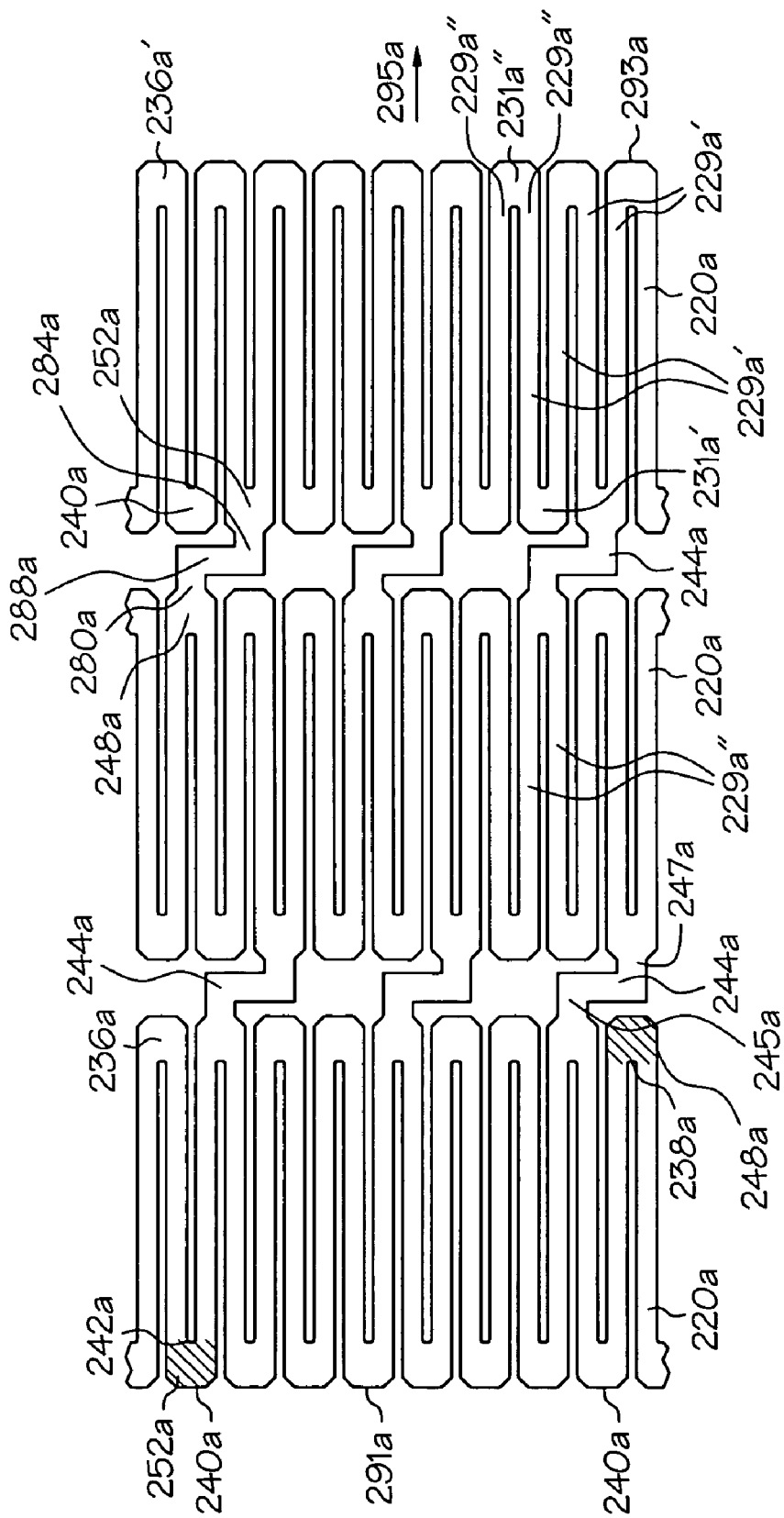
FIG. 4a shows a flat view of a stent configuration according to the invention.
Figure 4B:
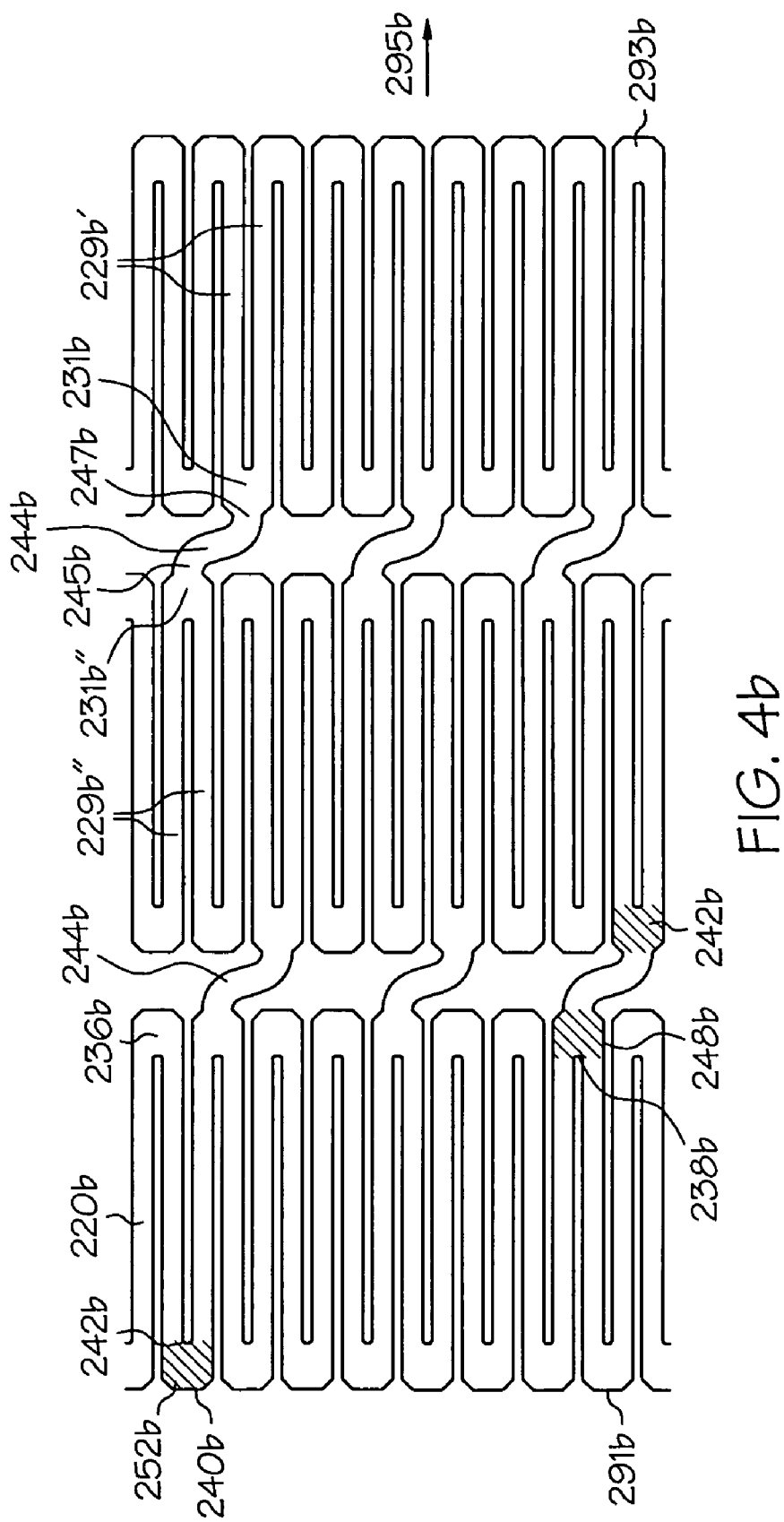
FIG. 4b shows a flat view of a stent configuration according to the invention.

In another embodiment, the inventive stent is comprised of band-like elements of a single wavelength, interconnected by interconnecting elements. Turning to FIGS. 4*a* and 4*b*, band-like elements 220*a,b* are interconnected by interconnecting elements 244*a,b*. Adjacent band-like elements 220*a,b* are 180° out of phase with one another. In the compressed state, the band-like elements consist of a plurality of peaks 236*a,b* and troughs 240*a,b*. Peak region 248*a,b* and trough region 252*a,b* have been shaded in one instance for illustrative purposes.

In the embodiment shown in FIG. 4*a*, each interconnecting element 244*a* extends between a peak region 248*a* and a trough region 252*a*. Rectilinear interconnecting elements 244*a* consist of a first shank 280*a*, a second shank 284*a* and a link 288*a* disposed in-between the first and second shanks 280*a* and 284*a*. First shank 280*a* extends in a longitudinal direction from peak region 248*a* and is substantially perpendicular to link 288*a*. Second shank 284*a* extends in a longitudinal direction from trough region 252*a* and is perpendicular to link 288*a*.

In the embodiment shown in FIG. 4*b*, the stent differs from the embodiment of FIG. 4*a* in that interconnecting element 244*b* extending between a peak region 248*b* and a trough region 252*b* is curvilinear rather than rectilinear.

In both FIGS. 4*a* and 4*b*, the interconnecting elements are seen to emanate from the middle of the peak and trough regions.

Figure 5A:
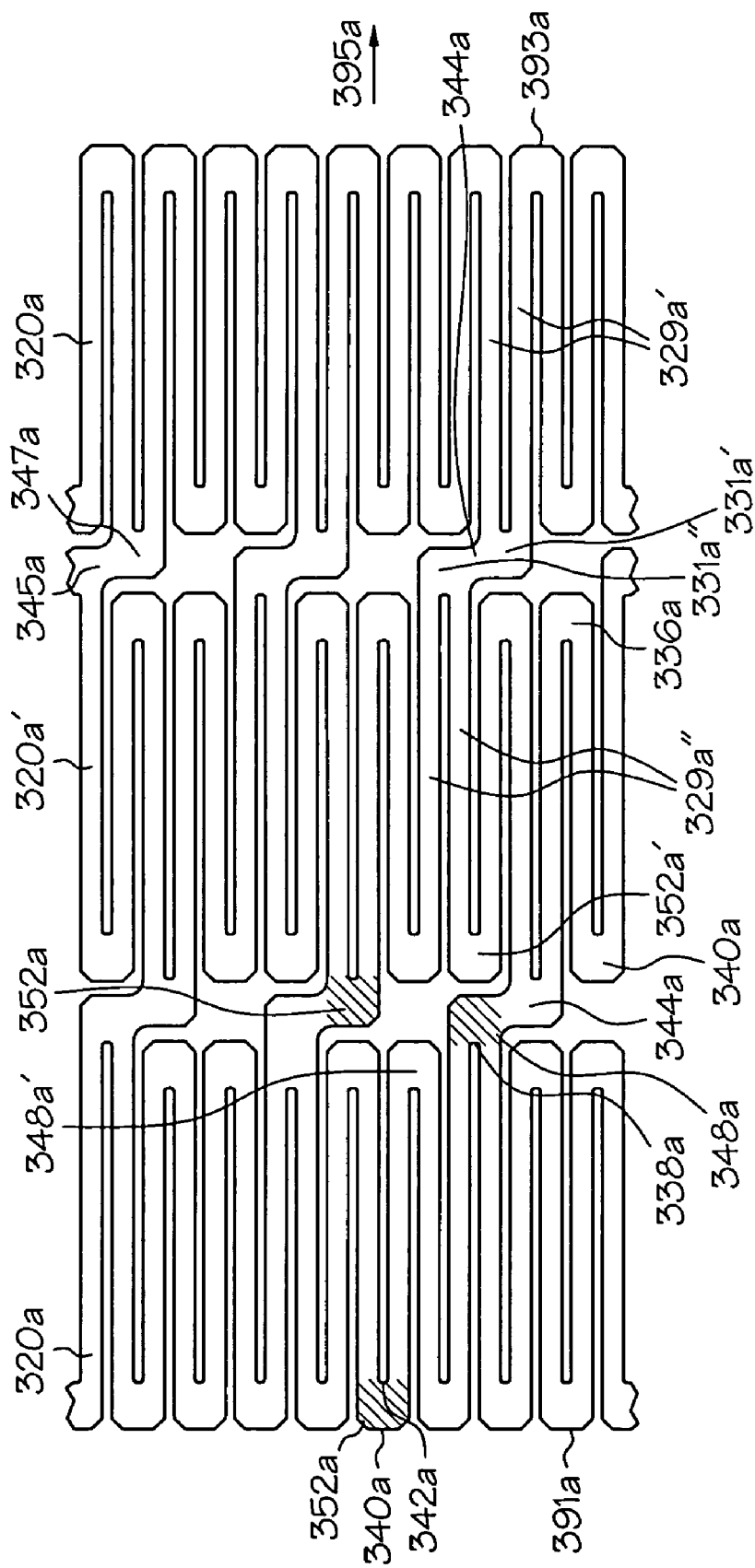
FIG. 5a shows a flat view of a stent configuration according to the invention.

In another embodiment, as shown in FIG. 5*a*, the inventive stent is comprised of band-like elements 320*a* of a single wavelength, interconnected by interconnecting elements 344*a*. Adjacent band-like elements 320*a* are 180° out of phase with one another. The band-like elements consist of a plurality of peaks 336*a* and troughs 340*a*. Interconnecting elements 344*a* extend between a peak region 348*a* and a trough region 352*a*. The peak regions 348*a* and trough regions 352*a* from which interconnecting elements 344*a* emanate on a given band-like element 320*a* are seen to extend longitudinally beyond adjacent peak regions 348*a*' and trough regions 352*a*' from which no interconnecting elements extend. The extension is such that at least a portion of peak regions 348*a* overlap longitudinally along the stent with at least a portion of trough region 352*a* on an adjacent band-like element 320*a*'. Of course, the overlap is limited to the longitudinal direction and not to the circumferential direction.

In another embodiment, as shown in FIG. 5b, interconnecting elements 344b extend between peak region 348b and a second closest trough region 352b on an adjacent band-like element. Interconnecting elements 344b are seen to be perpendicular to the longitudinal axis. As in the stent of FIG. 5a, peak regions 348b from which interconnecting elements 344b extend and trough regions 352b from which interconnecting elements 344b extend may extend beyond adjacent peak regions 348b' and trough regions 352b' from which no interconnecting elements 344b emanates.

Figure 6:
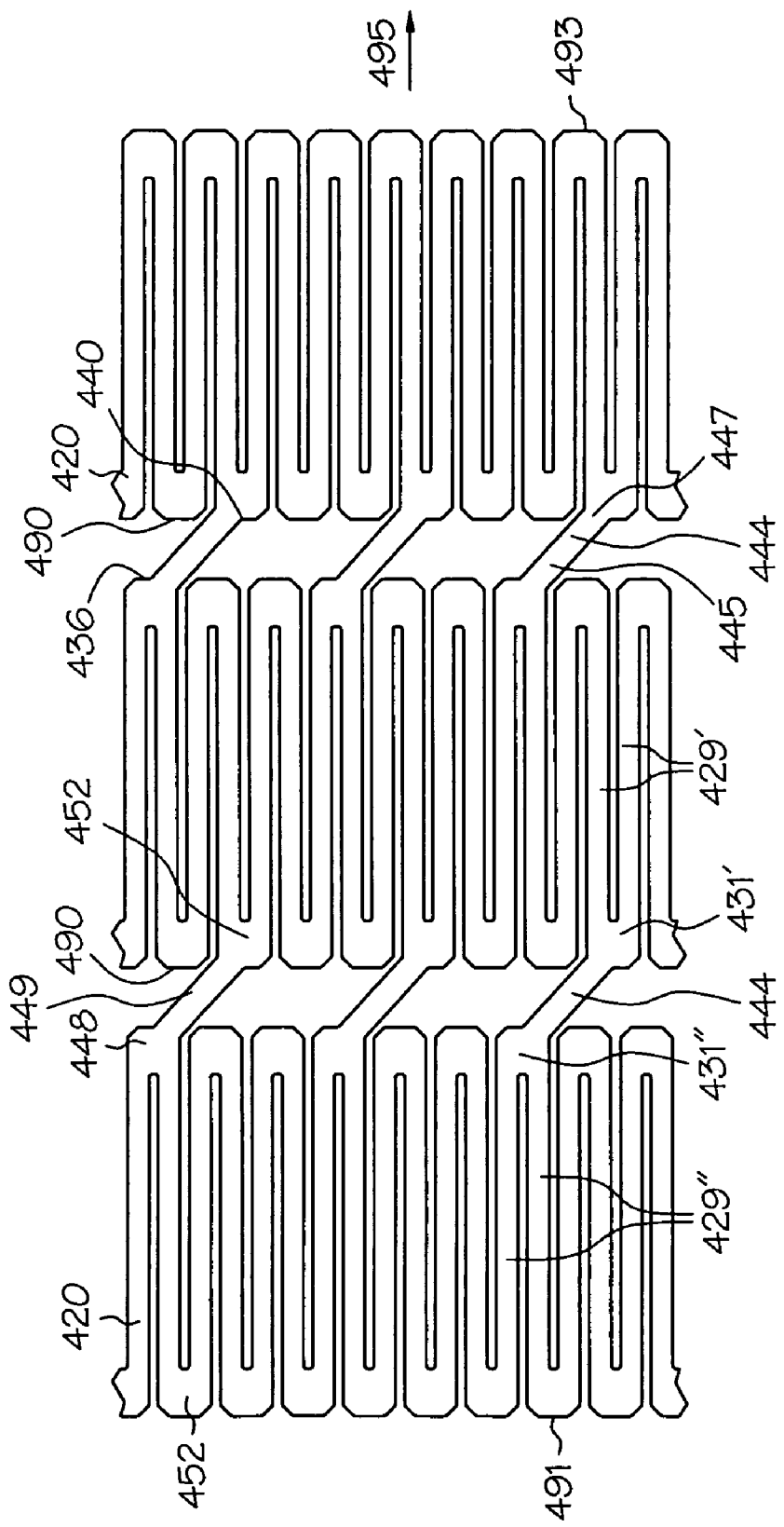
FIG. 6 shows a flat view of a stent configuration according to the invention.

In another embodiment, as shown in FIG. 6, adjacent band-like elements 420 are in phase with each other. As in previous Figs, band-like elements 420 are of a single wavelength, interconnected by interconnecting elements 444. The band-like elements consist of a plurality of peaks 436 and troughs 440. Interconnecting elements 444 extend at an oblique angle relative to the longitudinal axis of the stent between a peak region 448 and a trough region 452. As such, ends of interconnecting elements 444 are circumferentially offset relative to each other. The exact angle will, of course, depend on the region from which the interconnecting elements extend, as well as on whether interconnecting elements interconnect nearest peaks and troughs, next nearest peaks and troughs or peaks and troughs that are further separated.

In FIGS. 5a, 5b and 6, the interconnecting elements are seen to emanate from the sides of the peak and trough regions.

Figure 7:
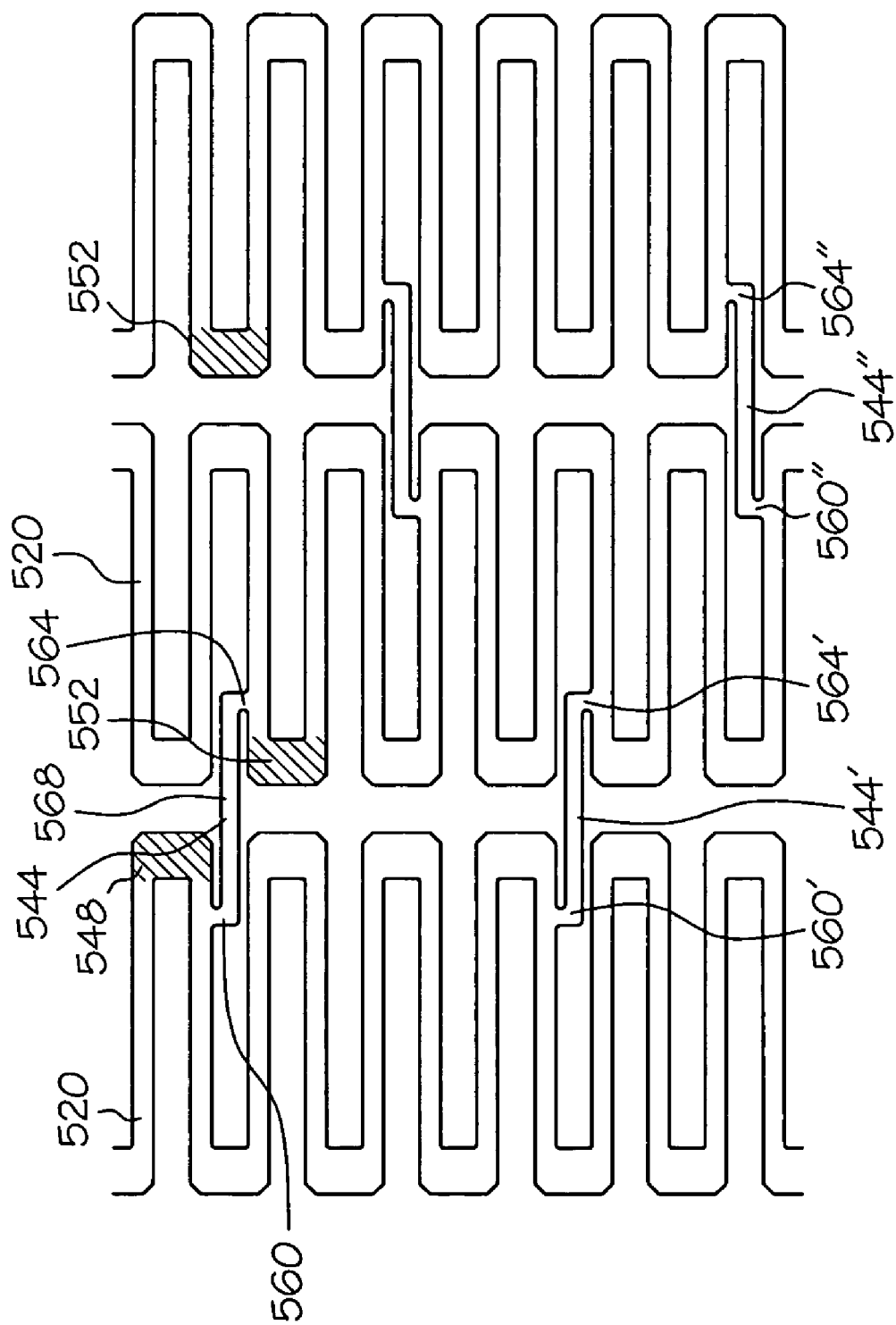
FIG. 7 shows a flat view of a stent configuration according to the invention.

Although for the embodiments of FIGS. 1-6, the interconnecting elements extend from peak regions on band-like elements to trough regions on adjacent band-like elements, the invention further contemplates interconnecting elements extending from a position between a peak region and an adjacent trough region on a band-like element to a position intermediate a trough region and a peak region on an adjacent second band-like element as in FIG. 7.

In the embodiment of FIG. 7, interconnecting elements are seen to extend from a region between the peak region and the trough region on a band-like element. The stent is formed of adjacent band-like elements 520 which are 180° degrees out of phase with one another. Interconnecting elements 544 extend from a region intermediate a peak region 548 and a trough region 552 on a band-like element to a region intermediate a peak region 548 and a trough region 552 on an adjacent band-like element. Interconnecting elements 544 consist of a first shank 560, a second shank 564, and an intermediate member 568 disposed in-between first and second shanks 560 and 564. First shank 560 and second shank 564 are substantially perpendicular to intermediate member 568 which extends in the longitudinal direction. Although not depicted, the region from which interconnecting elements 544 emanate may be midway between peaks and troughs.

The embodiment of FIG. 7 also differs from the embodiments of FIGS. 2-6 in the orientation of the interconnecting elements. Whereas the interconnecting elements in FIGS. 2-6 are all similarly oriented, in the embodiment of FIG. 7, the orientation of interconnecting elements alternates between adjacent pairs of adjacent band-like elements. Specifically, second shanks 564' of interconnecting elements 544' are seen to be displaced in a clockwise circumferential direction along the stent relative to first shanks 560', and seconds shank 564" of interconnecting elements 544" are seen to be displaced in a counterclockwise circumferential direction along the stent relative to while first shank 560".

Figure 8:
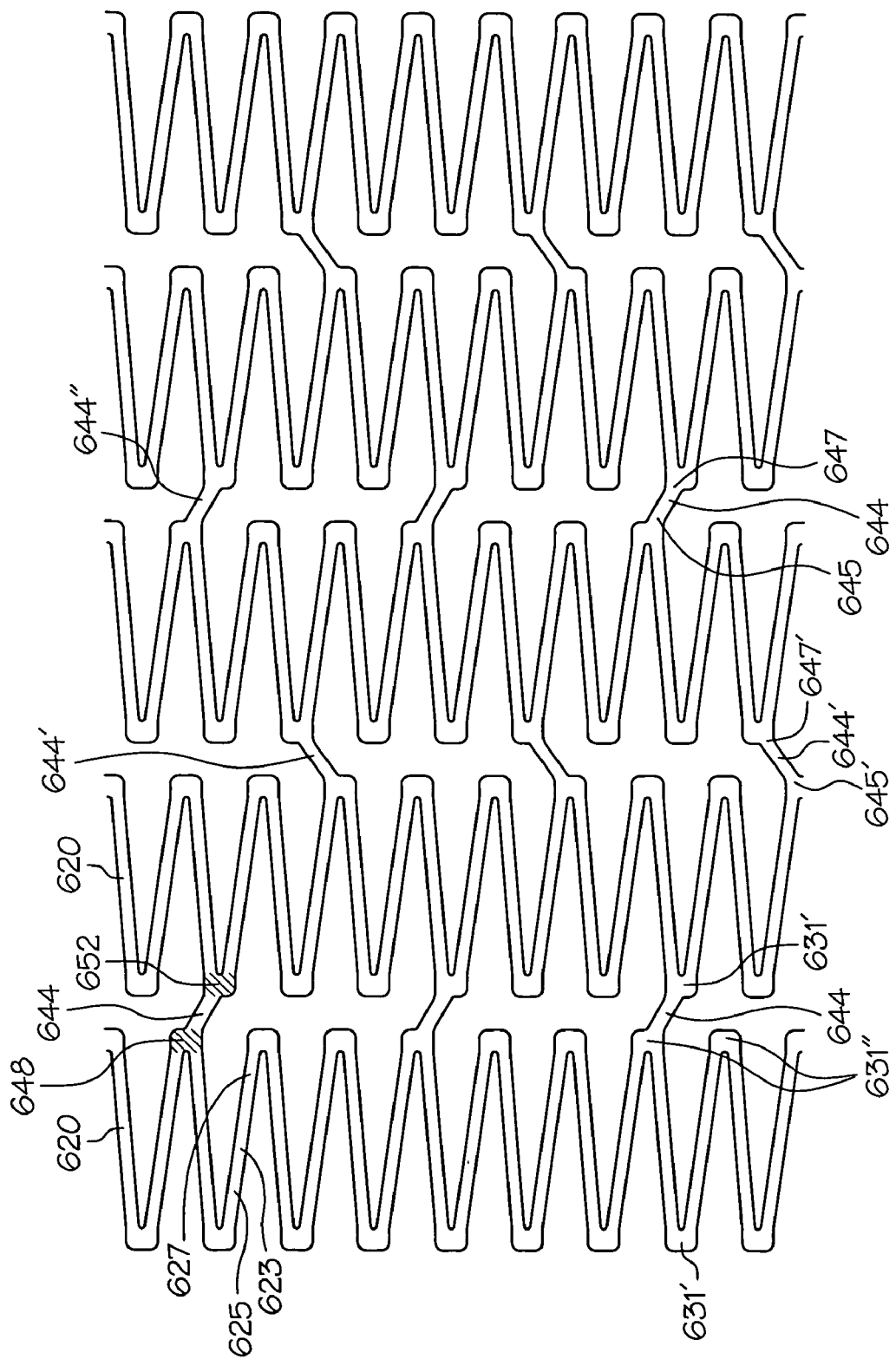
FIG. 8 shows a flat view of a stent configuration according to the invention.

This feature is also seen in the embodiment of FIG. 8 in which adjacent in-phase band-like elements 620 are interconnected by interconnecting elements 644. Interconnecting elements 644 extend at an oblique angle relative to the longitudinal axis of the stent between a peak region 648 and a trough region 652. As in FIG. 7, the orientation of interconnecting elements alternates between adjacent pairs of adjacent band-like elements. Specifically, the distal ends of interconnecting elements 644' are seen to be oriented in a counterclockwise circumferential direction along the stent relative to the proximal end of the interconnecting elements while the distal ends of interconnecting elements 644" are seen to be displaced in a clockwise circumferential direction along the stent relative to the proximal ends.

Although in the embodiments of FIGS. 2-8, adjacent bands are connected by five interconnecting elements, additional or fewer interconnecting elements may be used. Further, while interconnecting elements are shown spaced three peaks apart and three troughs apart, other separations are contemplated as well.

Figure 9:
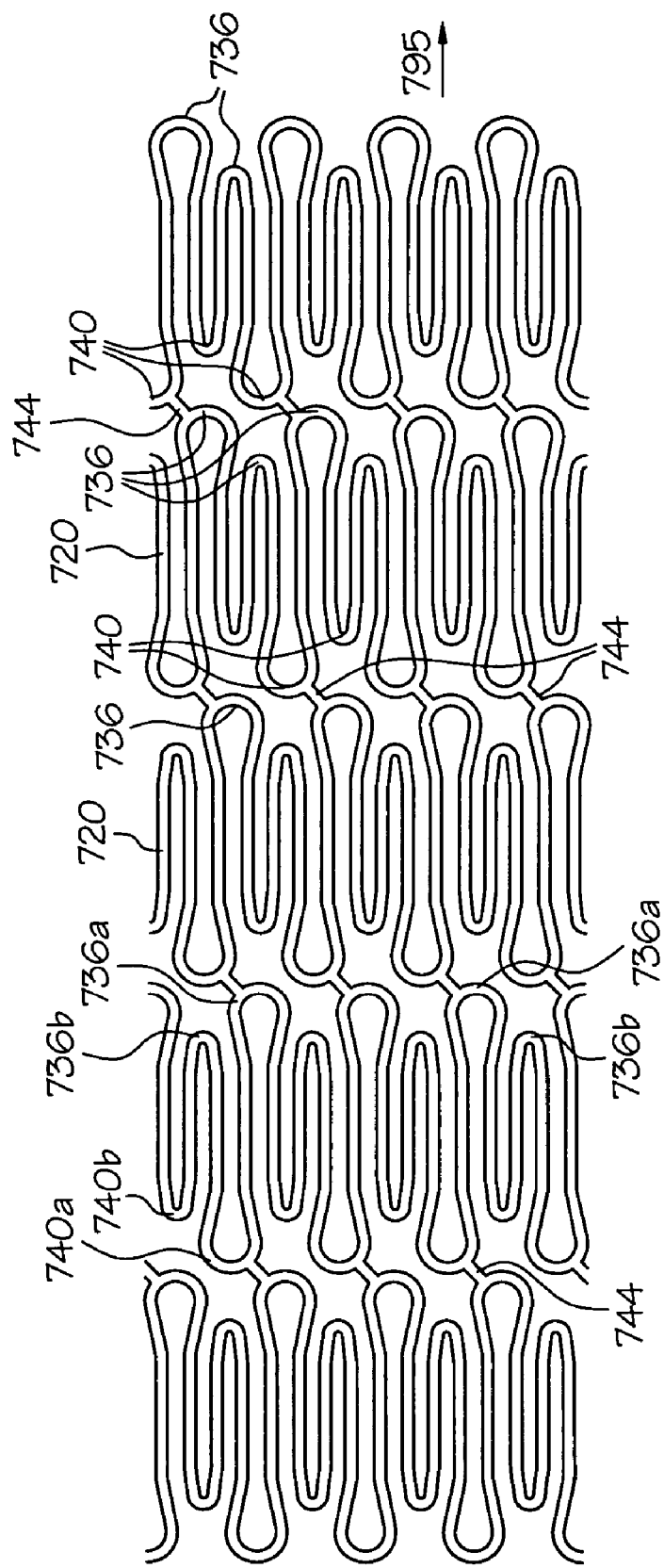
FIG. 9 shows a flat view of a stent configuration according to the invention.

In the embodiment of FIG. 9, each band-like element 720 is seen to comprise peaks 736 of more than one amplitude and troughs 740 of more than one amplitude. Large amplitude peaks 736a and small amplitude peaks 736b alternate as do large amplitude troughs 740a and small amplitude troughs 740b. As in the previous embodiments, the interconnecting elements are oriented at an oblique angle relative to the longitudinal axis 795 of the stent. More generally, the invention is directed at stents comprising band-like elements whose amplitude varies along the band-like element.

Figure 10:
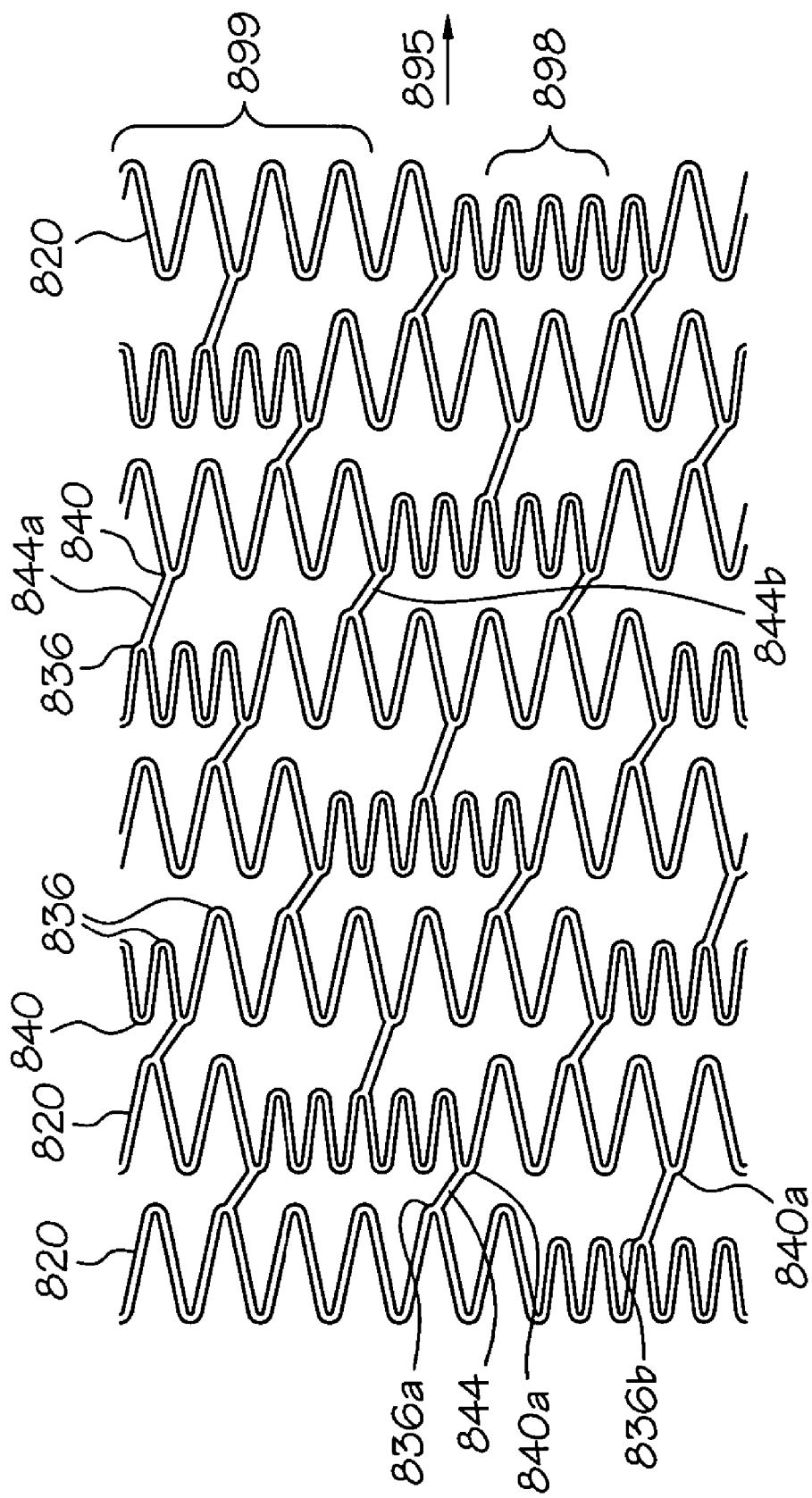
FIG. 10 shows a flat view of a stent configuration according to the invention.

In another embodiment of the invention, as shown in FIG. 10, each band-like element 820 is seen to comprise peaks 836 of more than one amplitude and troughs 840 of more than one amplitude, however, peaks of the same amplitude are grouped together within a band-like element as are troughs of the same amplitude. It is further noted that in the embodiment of FIG. 10, the location of a group of peaks of given amplitude in a band-like element varies circumferentially along the length of the stent. Interconnecting elements 844 connect peaks 836 and troughs 840 in adjacent band-like elements 820. Where several peaks of different amplitudes are present in a band-like element, the invention further contemplates the possibility of interconnecting elements extending from the large peaks 836a to large troughs 840a as in FIG. 9 as well as the possibility of interconnecting elements extending from large peaks to small troughs or from small peaks 836b to large troughs 840a as in FIG. 10. Further, the interconnecting elements between any two adjacent band-like elements may be of different lengths from one another as seen in FIG. 10 and commence at different longitudinal positions within a band-like element and terminate at different longitudinal positions within a band-like element. Interconnecting element 844a is seen to be longer than interconnecting element 844b. As in the previous embodiments, the interconnecting elements are oriented at an oblique angle relative to the longitudinal axis 895 of the stent. In the embodiment of FIG. 10, interconnecting element 844a is seen to be oriented at a smaller oblique angle relative to the longitudinal axis of the stent than interconnecting element 844b. As is apparent from FIG. 10, the invention is also directed to stents comprised of band-like elements whose wavelength varies along a given band-like element. Region 898 and region 899 of band-like element are characterized by different wavelengths.

It is also noted that in the embodiment of FIG. 10, all of the troughs 840a,b in a given band-like element 820 are aligned longitudinally along the stent and differ only in their circumferential position along the stent.

It is further noted in the embodiment of FIG. 10, the stent comprises a first group of interconnecting elements 844a and a second group of interconnecting elements 844b. The interconnecting elements of the first group are all parallel to one another and disposed at a different oblique angle relative to the longitudinal axis than the members of the second group which are all parallel to one another. As such, the invention contemplates stents having several different groups of obliquely disposed interconnecting elements where the oblique angle differs from group to group.

Figure 11:
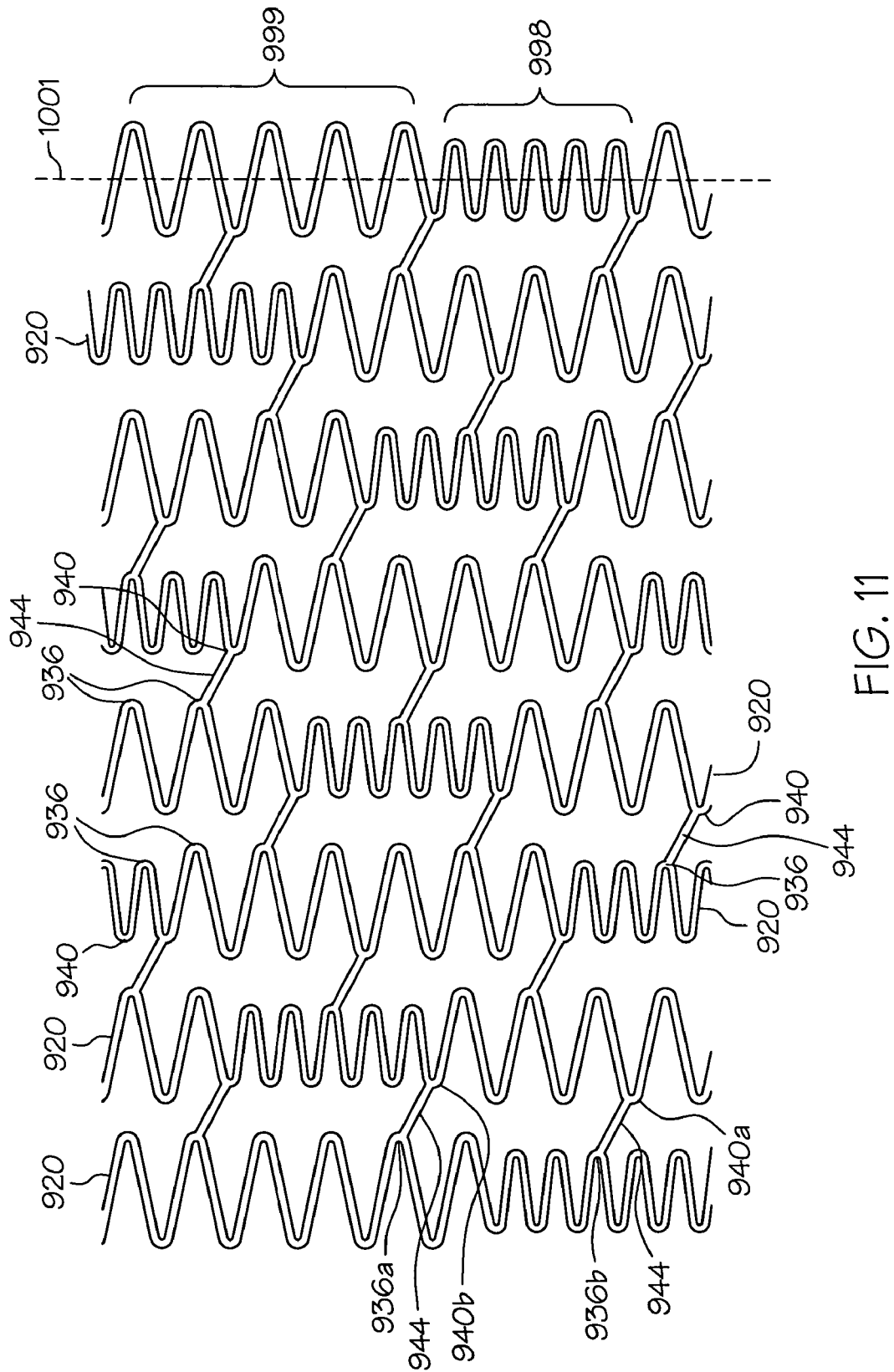
FIG. 11 shows a flat view of a stent configuration according to the invention.

In another embodiment of the invention, as shown in FIG. 11, each band-like element 920 is seen to comprise peaks 936a,b of different amplitudes and troughs 940 of different amplitudes, however, peaks of the same amplitude are grouped together within a band-like element as are troughs of the same amplitude. It is further noted that in the embodiment of FIG. 11 the location of groups of peaks of given amplitude in a band-like element varies circumferentially along the length of the stent. Interconnecting elements 944 connect large amplitude peaks 936a and small amplitude troughs 940b in adjacent band-like elements 920. Similarly, interconnecting elements 944 also connect small amplitude peaks 936b and large amplitude troughs 940a.

The invention also contemplates stents similar to that shown in FIG. 11 in which interconnecting elements extend from large peaks 936a to large troughs 940a, as in FIG. 9. Similarly, interconnecting elements may extend from small peaks 936b to small troughs 940b.

Further, the interconnecting elements between any two adjacent band-like elements may be of different lengths from one another and disposed at different oblique angles.

As is apparent from FIG. 11, the invention is also directed to stents comprised of band-like elements whose wavelength varies along a given band-like element. Region 998 and region 999 of band-like element 920 are characterized by different wavelengths.

It is also noted that in the embodiment of FIG. 11 the large amplitude portions 999 of band-like element 920 are symmetrically disposed about the center 1001 of the band-like element as are the small amplitude portions 998. The center 1001 of the band-like element is defined as a ring that runs along a path that is midway between the large peaks 936a and large troughs 940a of the band-like element. This feature may also be seen in the embodiment of FIG. 9.

The invention is also directed to a tubular, flexible, expandable stent having a longitudinal axis, comprising one or more cylindrical shaped first segments. Cylindrical shaped first segments 20 as seen in FIG. 1, have first struts 23 having first 25 and second 27 ends. First segments 20 are defined by a member formed in an undulating pattern of interconnected paired first struts 23, in which adjacent pairs of first struts 29' and 29" in a given first segment 20 are interconnected at opposite ends 31' and 31", respectively. Adjacent segments are interconnected.

The stent may be seen more clearly in FIGS. 2-8. As shown, the stent of FIG. 3, in addition to comprising first segments 120 which are defined by an undulating pattern of interconnected paired first struts 123 in which adjacent pairs of first struts 129' and 129" in a given first segment 120 are interconnected at opposite ends 131' and 131", respectively, the stent further comprises one or more cylindrical shaped second segments 132, each second segment being defined by a member formed in an undulating pattern of interconnected paired second struts 135 and in which adjacent pairs of second struts 137' and 137" in a given second segment 132 are interconnected at opposite ends 139' and 139", respectively. First struts 123 are shorter than second struts 135. First segments 120 are formed of a number of first struts 123 and second segments 132 formed of a number of second struts 135, the number of first struts in a first segment exceeding the number of second struts in a second segment. First and second segments 120 and 132 are aligned on a common longitudinal axis 195 to define a generally tubular stent body, shown generally at 115. First and second segments 120 and 132 alternate along the stent body. Adjacent first and second segments 120 and 132 are connected by a plurality of interconnecting elements 144. Each interconnecting element 144 extends from an end 131" of paired first struts on a first segment 120 to an end 139" of paired second struts on an adjacent second segment 132. The ends of interconnecting elements 144 are circumferentially offset relative to each other.

Desirably, upon expansion of stent 115, paired struts 129" and 137" of adjacent segments 120 and 132 are displaced relative to each other about the periphery of the stent body to accommodate longitudinal flexing of the stent within the segments and without interference between adjacent segments.

In the embodiments as shown in FIGS. 4a, b, cylindrical shaped segments 220a,b are formed of interconnected struts 223a,b having first 225 and second 227 ends. Adjacent pairs of struts 229a,b' and 229a,b" in a given segment 220a,b are interconnected at opposite ends 231a,b' and 231a,b", respectively. Adjacent segments are connected by a plurality of interconnecting elements 244a,b. Each interconnecting element 244a,b extends from an end of paired struts 231a,b" on a segment to an end of paired struts 231a,b' on an adjacent segment. First end 245a,b and second end 247a,b of interconnecting elements 244a,b are seen to be circumferentially displaced along the stent.

Similar structure, denoted by similar reference numerals may be found in the stents of FIGS. 5a,b, and 6-8.

In particular, in the embodiment as shown in FIG. 8, cylindrical shaped segments 620 are formed of interconnected struts 623, having first 625 and second 627 ends. Segments 620 are defined by a member formed in an undulating pattern of interconnected paired struts 623 in which adjacent pairs of struts 629' and 629" in a given segment 620 are interconnected at opposite ends 631' and 631", respectively. Segments 620 are aligned on a common longitudinal axis 695 to define a generally tubular stent body. Adjacent segments are connected by a plurality of interconnecting elements 644 (and 644') having first 645 (645') and second 647 (647') ends, each interconnecting element 644 (644') extending from an end of paired struts 631" on a segment to an end of paired struts 631' on an adjacent segment. First end 645 (645') and second end 647 (647") are seen to be circumferentially displaced along the stent.

Figure 12:
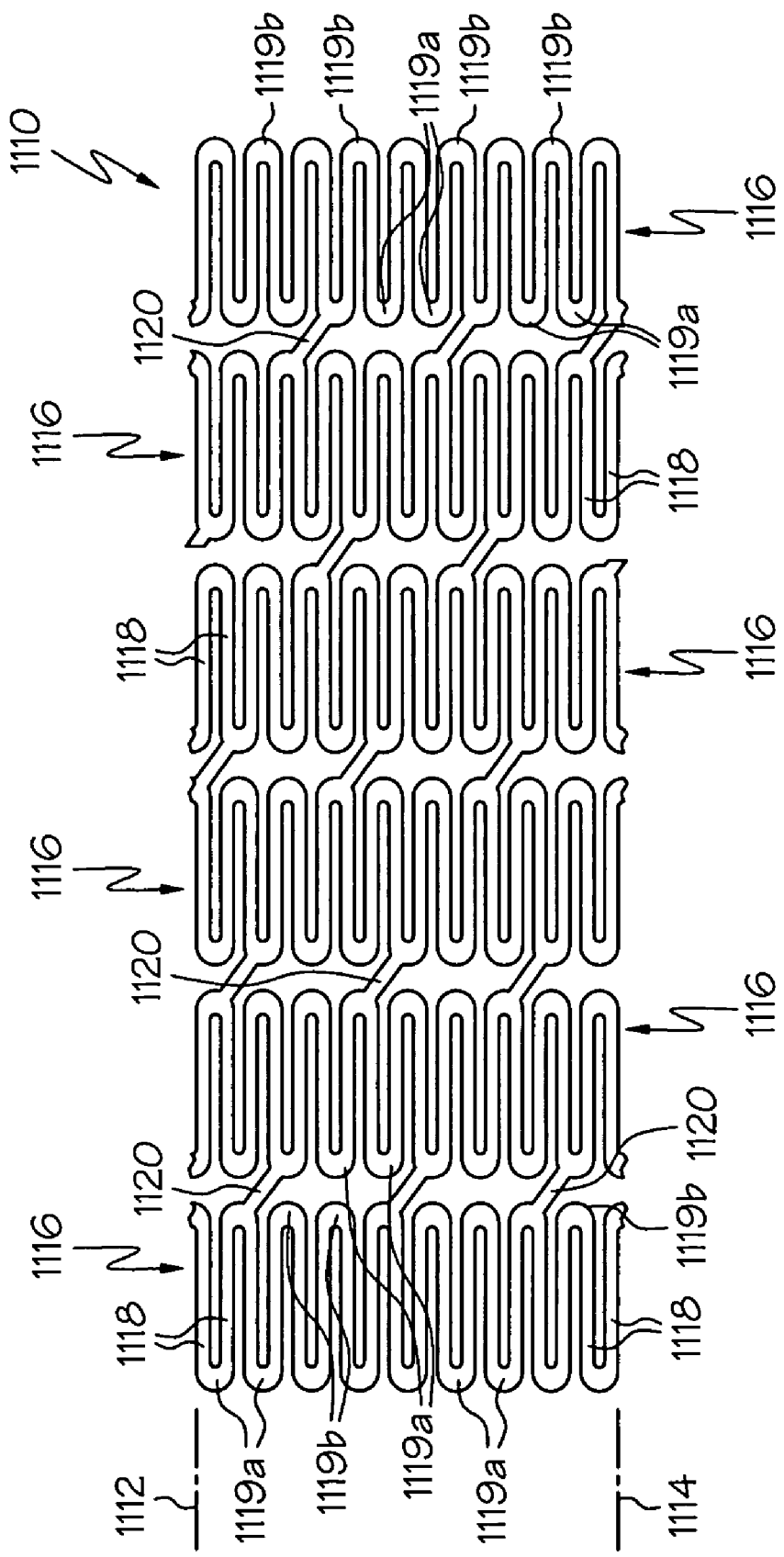
FIG. 12 shows a flat view of a stent configuration according to the invention.
Figure 13:
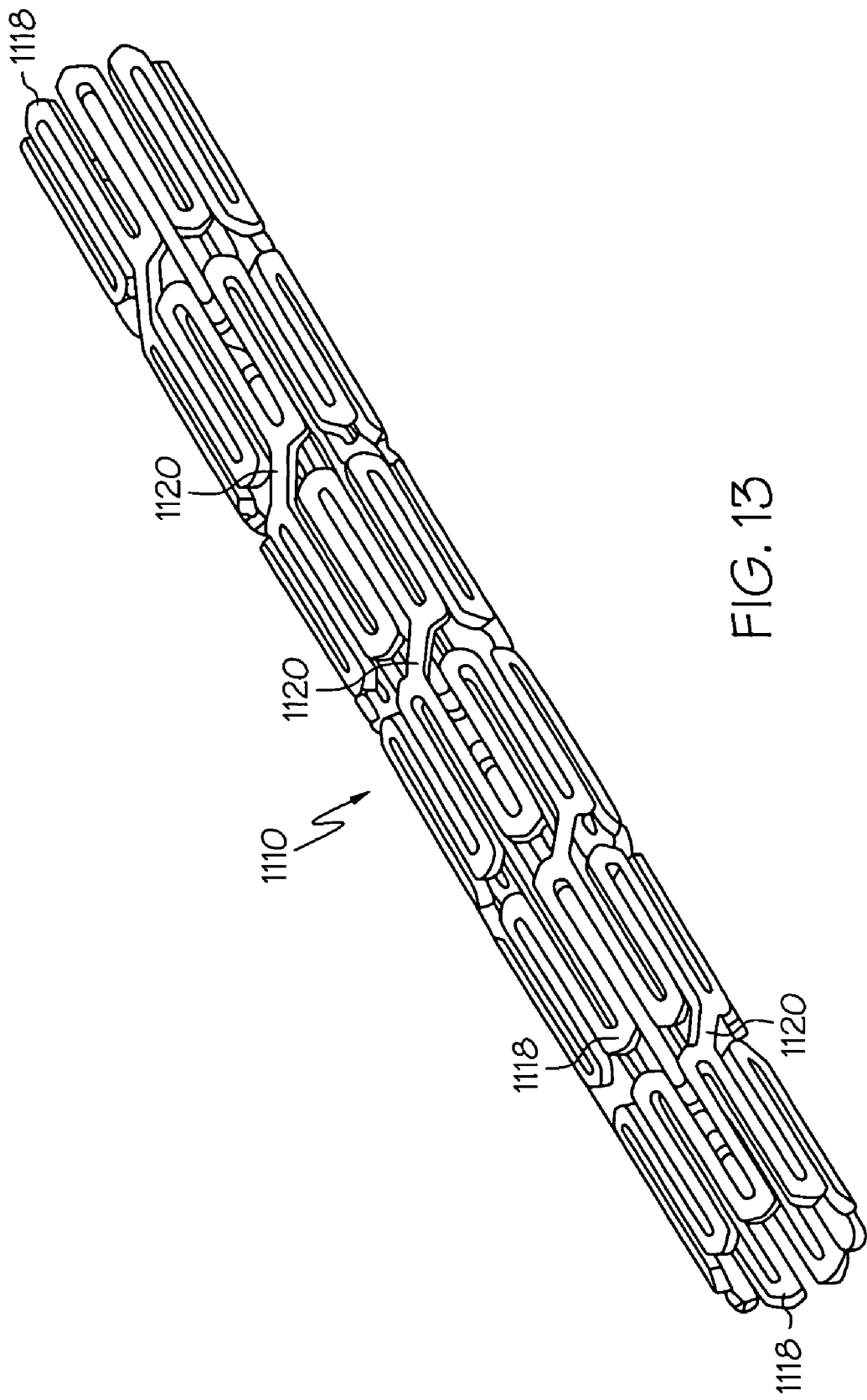
FIG. 13 shows the pattern of FIG. 12 in a tubular stent.

Additional embodiment of the stents are shown in FIGS. 12-15. FIG. 12 and FIG. 13 show a fragmentary flat view of an unexpanded stent configuration and the actual tubular stent (unexpanded), respectively. That is, the stent is shown for clarity in FIG. 12 in the flat and may be made from a flat pattern 1110 (FIG. 12) which is formed into a tubular shape by rolling the pattern so as to bring edges 1112 and 1114 together (FIG. 12). The edges may then joined as by welding or the like to provide a configuration such as that shown in FIG. 13.

The configuration can be seen in these Figures to be made up of a plurality of adjacent segments generally indicated at 1116, each of which is formed in an undulating flexible pattern of substantially parallel struts 1118. Pairs of struts are interconnected at alternating end portions 1119a and 1119b. As is seen in FIG. 12, the interconnecting end portions 1119b of one segment are positioned opposite interconnecting end portions 1119a of adjacent segments. The end portions as shown are generally elliptical but may be rounded or square or pointed or the like. Any configuration of end portions is acceptable so long as it provides an undulating pattern, as shown. When the flat form 1110 is formed into an unexpanded tube as shown in FIG. 13, the segments are cylindrical but the end portions 1119 of adjacent segments remain in an opposed position relative to each other.

A more preferred method of manufacture begins with a thin walled tube which is then laser cut to provide the desired configuration. It may also be chemically etched or EDM'd (electrical discharge machined) to form an appropriate configuration.

Interconnecting elements 1120 extend from one end portion 1119 of one segment 1116 to another end portion 1119 of another adjacent segment 1116 but not to an oppositely positioned end portion 1119 of an adjacent segment 1116. There are at least three struts included between the points on each side of a segment 1116 at which an interconnecting element 1120 contacts an end portion 1119. This results in the interconnecting elements 1120 extending in an angular direction between segments around the periphery of the tubular stent. Interconnecting elements 1120 are preferably of the same length but may vary from one segment to the other. Also, the diagonal direction may reverse from one segment to another extending upwardly in one case and downwardly in another, although all connecting elements between any pair of segments are substantially parallel. FIG. 12, for example shows them extending downwardly, right to left. Upwardly would extend up left to right in this configuration.

Figure 14:
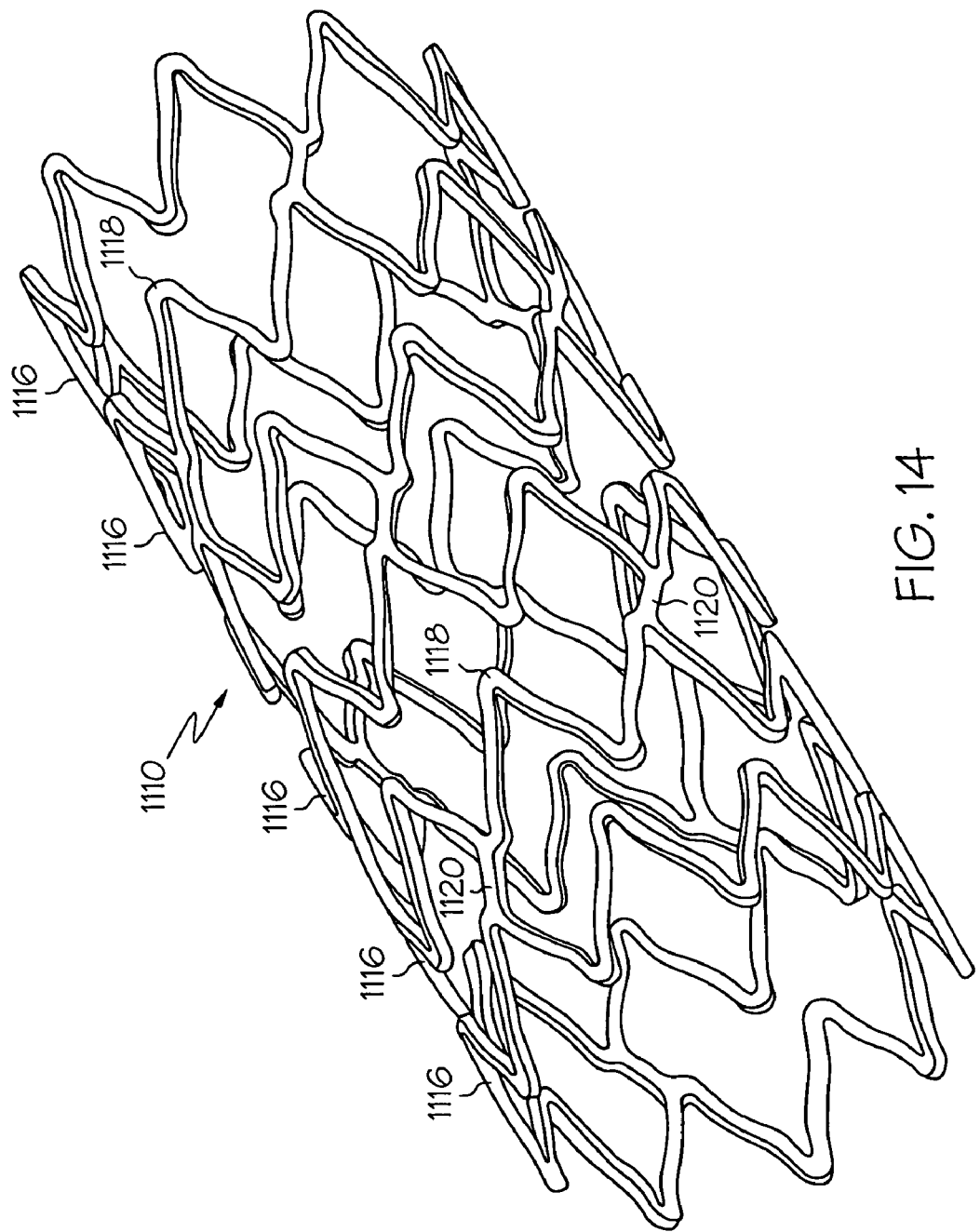
FIG. 14 shows an expanded stent of the configuration shown in FIG. 12.

As a result of this angular extension of the interconnecting elements 1120 between adjacent segments and loops, upon expansion of the stent as seen in FIG. 14, the closest adjacent end portions 1119 between segments 1116 are displaced from each other and are no longer opposite each other so as to minimize the possibility of binding or overlapping between segments, i.e., pinching.

The number of interconnecting elements 1120 may vary depending on circumstances in any particular instance. Three per segment are satisfactory for the configuration shown and at least three will be used typically.

Figure 15:
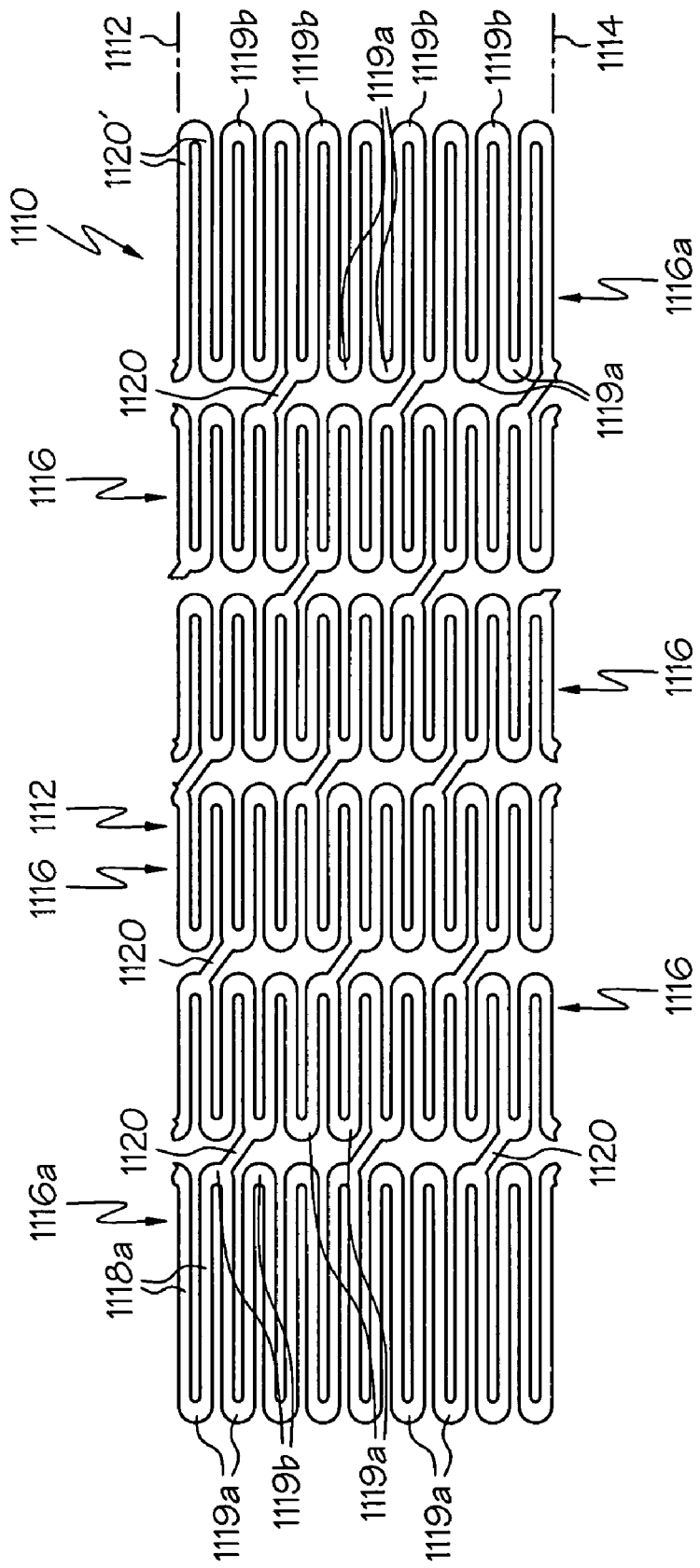
FIG. 15 shows a flat view of an alternate stent configuration according to the invention.

The alternate design shown in FIG. 15 includes longer struts 1118a in the two end segments 1116a than in the intermediate segments 1116. This allows the end segments (1116a) to have less compression resistance than the intermediate segments (1116), providing a more gradual transition from the native vessel to the support structure of the stent. Otherwise, the configuration is the same as that shown in FIG. 12.

As indicated in the Figures, the invention contemplates a variation of interconnecting element shapes ranging from rectilinear to curvilinear. The invention further contemplates embodiments in which all interconnecting elements are similarly oriented as well as embodiments in which adjacent sets of interconnecting elements extending between adjacent pairs of segments are oppositely oriented (e.g., FIGS. 7 and 8). The invention also contemplates the use of interconnecting elements which extend from a range of positions along the segments, ranging from various positions in the area in which paired struts are interconnected to other positions along the struts.

The invention also contemplates the possibility of interconnecting elements extending at an oblique angle relative to the longitudinal axis of the stent and connecting adjacent peaks and troughs on adjacent segments as well as peaks and troughs on adjacent segments which are separated by one or more peaks and/or troughs.

The invention also contemplates reversing the orientation of interconnecting elements as shown in FIGS. 7 and 8.

Finally, there are preferably at least three interconnecting elements joining adjacent first and second segments although fewer or additional interconnecting elements are also contemplated.

It is understood that the peaks and troughs of the present invention need not be rounded, as shown in the Figures. The peaks and troughs may be bulbous, triangular, square, pointed, or otherwise formed of interconnected straight sections.

As already indicated, this invention is applicable to self-expanding configurations, mechanically expandable configurations and to a wide variety of materials, including both metal and plastic and any other material capable of functioning as an expandable stent. For example, the stent may be of metal wire or ribbon such as tantalum, stainless steel or the like. It may be thin-walled. It may be of shape memory alloy such as Nitinol or the like, etc. The interconnecting elements may be formed integrally with the band-like elements (or segments) or may be bonded thereto via such methods as adhesive bonding, welding or any other known method of bonding.

The above Examples and disclosure are intended to be illustrative and not exhaustive. These examples and this description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is as follows:

1. A stent in the form of a thin-walled, cylindrical tube with a longitudinal axis, the stent comprising:
   a multiplicity of interior circumferential sets of strut members and one end circumferential set of strut members at each of the two longitudinal ends of the stent, each interior circumferential set of strut members and each end circumferential set of strut members having a first end and a second end;
   each interior circumferential set of strut members including a plurality of strut members connected by curved sections, the plurality of strut members including long strut members and short strut members, at least two of the long strut members being attached to one another by one of the curved sections, the curved sections located at the first and second ends, the curved sections including connected curved sections and unconnected curved sections, each two adjacent strut members connected by a single curved section,
   the strut members including at least one connected strut member consisting of a long diagonal section having a longitudinal length fixedly attached to a connected curved section,
   each connected curved section being joined by a longitudinal connecting link to one connected curved section of an adjacent circumferential set of strut members, each connecting link that connects adjacent circumferential sets of strut members is connected at a connected curved section,
   the strut members also including at least one unconnected strut member consisting of a short diagonal section having a longitudinal length fixedly joined to an unconnected curved section.

2. The stent of claim 1 wherein the longitudinal connecting link is straight.

3. The stent of claim 1 wherein the longitudinal connecting link is an undulating, flexible, longitudinal connecting link.

4. The stent of claim 3 wherein the place where each flexible longitudinal connecting link is joined to the interior set of strut members is near the connecting line where a connected curved section is joined to a diagonal section.

5. The stent of claim 1 wherein there are three longitudinal connecting links that join each adjacent pair of circumferential sets of strut members.

6. The stent of claim 1 wherein there are five longitudinal connecting links that join each adjacent pair of circumferential sets of strut members.

7. The stent of claim 1 wherein the total longitudinal length in the longitudinal direction of each end circumferential set of strut members is shorter than the longitudinal length in the longitudinal direction of each interior circumferential set of strut members.

8. The stent of claim 1 wherein the stent is formed from stainless steel.

9. The stent of claim 1 wherein the stent is formed from tantalum.

10. The stent of claim 1, wherein each interior circumferential set of strut members has fewer connected curved sections than unconnected curved sections.

11. A cylindrical expandable stent comprising:
a plurality of undulating band-like elements aligned on a common longitudinal axis to define a generally tubular stent body having a first end and a second end, each band-like element having alternating peaks and troughs, the peaks and troughs taking a generally longitudinal direction along the cylinder,
the peaks of each band-like element comprising peaks of a first amplitude and peaks of a second amplitude, at least three peaks which are immediately circumferentially adjacent to one another having the second amplitude, the first amplitude being less than the second amplitude; and
a plurality of interconnecting elements, each interconnecting element having a first end and a second end, the first and second ends extending from adjacent band-like elements, the first and second ends displaced circumferentially along the stent.

12. The stent of claim 11, wherein peaks of the same amplitude are grouped together within a band-like element.

13. The stent of claim 12, wherein peaks having the first amplitude on a first band-like element are circumferentially offset from peaks having the first amplitude on a second band-like element.

14. The stent of claim 11, wherein each of the plurality of band-like elements has a first region having a first wavelength and a second region having a second wavelength, wherein the first wavelength is less than the second wavelength.

15. The stent of claim 14, wherein the first region comprises peaks having the first amplitude.

16. The stent of claim 11 wherein each of the plurality of interconnecting elements is substantially straight.

17. The stent of claim 11, wherein the plurality of interconnecting elements is comprised of first interconnecting elements having a first length and second interconnecting elements having a second length, wherein the first length is longer than the second length.

18. The stent of claim 17, wherein interconnecting elements having a first length extend from the peaks having the first amplitude on a band-like element to a trough on an adjacent band-like element.

19. The stent of claim 11 wherein the peaks of the second amplitude extend further toward the first end of the stent than the peaks of the first amplitude.

20. A stent comprising:
a multiplicity of interior sets of strut members, each interior set having a first end and a second end and a plurality of strut members which are connected one to the other, adjacent strut members within an interior set arranged in pairs of strut members wherein some of the strut pairs include a longer strut member and a shorter strut member and some of the strut pairs include two longer strut members, adjacent interior sets connected to one another via interconnecting elements,
wherein the interconnecting elements are arranged such that each interconnecting element which connects to an interior set adjacent the first end of the interconnecting element is connected to another interconnecting element which connects to the interior set adjacent the second end of the another interconnecting element via a pathway of only three connected strut members of the interior set.

21. The stent of claim 20 wherein some of the interconnecting members extend from the strut pairs having a longer strut member and a shorter strut member.

22. The stent of claim 21 wherein the first and second ends of each interconnecting member are circumferentially and longitudinally offset from one another.

23. The stent of claim 20 wherein said pathway includes two strut members of one length and one strut member of a different length.

* * * * *